US008224580B2

(12) United States Patent
Mundorff et al.

(10) Patent No.: US 8,224,580 B2
(45) Date of Patent: Jul. 17, 2012

(54) OPTIMIZATION OF CROSSOVER POINTS FOR DIRECTED EVOLUTION

(75) Inventors: Emily C. Mundorff, Milwaukie, OR (US); Sridhar Govindarajan, Redwood City, CA (US); Claes Gustafsson, Belmont, CA (US); Jeremy S. Minshull, Los Altos, CA (US)

(73) Assignee: Codexis Mayflower Holdings LLC, Redwood City, CA (US)

( * ) Notice: Subject to any disclaimer, the term of this patent is extended or adjusted under 35 U.S.C. 154(b) by 1422 days.

(21) Appl. No.: 11/818,237

(22) Filed: Jun. 12, 2007

(65) Prior Publication Data

US 2008/0020397 A1    Jan. 24, 2008

Related U.S. Application Data

(62) Division of application No. 10/386,903, filed on Mar. 10, 2003, now Pat. No. 7,620,500.

(60) Provisional application No. 60/363,505, filed on Mar. 9, 2002, provisional application No. 60/373,591, filed on Apr. 18, 2002.

(51) Int. Cl.
*G01N 33/48* (2006.01)
*G06F 19/00* (2011.01)

(52) U.S. Cl. .......................................... 702/19; 702/20

(58) Field of Classification Search .................. None
See application file for complete search history.

(56) References Cited

U.S. PATENT DOCUMENTS

| | | | |
|---|---|---|---|
| 5,198,346 | A | 3/1993 | Ladner et al. |
| 5,223,409 | A | 6/1993 | Ladner et al. |
| 5,741,691 | A | 4/1998 | Arnold et al. |
| 6,107,073 | A | 8/2000 | Chen |
| 6,109,776 | A | 8/2000 | Haas |
| 6,323,030 | B1 | 11/2001 | Stemmer |
| 6,365,408 | B1 | 4/2002 | Stemmer |
| 6,518,065 | B1 | 2/2003 | Stemmer |
| 7,620,500 | B2 | 11/2009 | Mundorff et al. |
| 8,108,150 | B2 | 1/2012 | Mundorff et al. |
| 2002/0045175 | A1 | 4/2002 | Wang et al. |
| 2003/0032059 | A1 | 2/2003 | Wang et al. |
| 2010/0070192 | A1 | 3/2010 | Mundorff et al. |

FOREIGN PATENT DOCUMENTS

| | | |
|---|---|---|
| WO | WO01/75767 | 10/2001 |
| WO | WO 01-90346 | 11/2001 |
| WO | WO 01/90346 A2 | 11/2001 |
| WO | WO03/055978 | 7/2003 |
| WO | WO 03/078583 A2 | 9/2003 |

OTHER PUBLICATIONS

Vendruscolo et al., "Recovery of protein structure from contact maps," (Folding and Design, vol. 2 (1997) pp. 295-306).*

"Fold Assembly of Small Proteins Using Monte Carlo Simulations Driven by Restraints Derived from Multiple Sequence Alignments," (J. Mol. Biol. (1998) vol. 277 pp. 419-448).*
U.S. Appl. No. 10/386,903, US Final Office Action mailed Jan. 9, 2008.
Konig et al., "Refined Genetic Algorithm Simulations to Model Proteins" Journal of Molecular Modeling vol. 5, 1999 pp. 317-324.
Japanese Office Action Mailed Feb. 19, 2010 from Application No. 2003-576577.
Park, "Toward an Energy Function for the Contact Map Representation of Proteins," Proteins: Structure, Function and Genetics 40:237-248 (2000).
Li et al., "Nature of Driving Force for Protein Folding: A Result from Analyzing the Statistical Potential," The American Physical Society, vol. 79, No. 4, 765-768 (1997).
Voigt et al., "Computationally Focusing the Directed Evolution of Proteins," Journal of Cellular Biochemistry Supplement, 37:58-63 (2001).
Skorobogatiy et al., "Mapping of Mutation-Sensitive Sites in Protein-like Chains," The American Physical Society, vol. 58, No. 3: 3572-2577 (1998).
Backofen et al., "Application of Constraint Programming Techniques for Structure Prediction of Lattice Proteins with Extended Alphabets," Bioinformatics, vol. 15, No. 3, 234-242 (1999).
Buchler et al., "Effect of Alphabet Size and Foldability Requirements on Protein Structure Designability," Proteins: Structure, Function and Genetics 34:113-124 (1999).
Gan et al., "Lattice Protein Folding with Two and Four-Body Statistical Potentials," Proteins: Structure, Function and Genetics 43:161-174 (2001).
Miyazawa et al., "Residue-Residue Potentials with a Favorable Contact Pair Term and an Unfavorable High Packing Density Term, for Simulation and Threading," J. Mol. Biol., 256:623-644 (1996).
Chao Zhang, "Extracting Contact Energies From Protein Structures: A Study Using a Simplified Model," Proteins: Structure, Function, and Genetics, 31:299-308 (1998).
Miyazawa et al., "Self-Consistent Estimation of Inter-Residue Protein Contact Engergies Based on an Equilibrium Mixture Approximation of Residues," Proteins: Structure, Function, and Genetics, 34:49-68 (1999).
Miyazawa et al., "An Empirical Energy Potential With a References State for Protein Fold and Sequence Recognition," Proteins: Structure, Function, and Genetics, 36:357-369 (1999).
Friesner et al., "Computer Simulation of Protein Folding," printed from http://www.chem.columbia.edu/cbs/protein/annrev/txt.html on Feb. 27, 2001, 15 Pages.
Voigt et al., "Calculating the Crossover Points for Gene Recombination and Hybrid Protein Creation," U.S. Appl. No. 60/201,048, filed May 23, 2000, 28 Pages.

(Continued)

*Primary Examiner* — Marjorie Moran
*Assistant Examiner* — Anna Skibinsky
(74) *Attorney, Agent, or Firm* — Weaver Austin Villeneuve & Sampson LLP

(57) ABSTRACT

Methods and devices for more efficiently engineering diversity into recombinant polypeptides and/or nucleic acids are provided herein. For example, a variety of methods of selecting and/or assessing potential crossover sites in an amino acid sequence or a nucleotide sequence are provided, as well as the resulting chimeric product sequences. These methods include, e.g., consideration of structural, functional and/or statistical data in the selection and assessment of sequences and crossover sites for use in recombination.

31 Claims, 4 Drawing Sheets

OTHER PUBLICATIONS

Figure 1A:
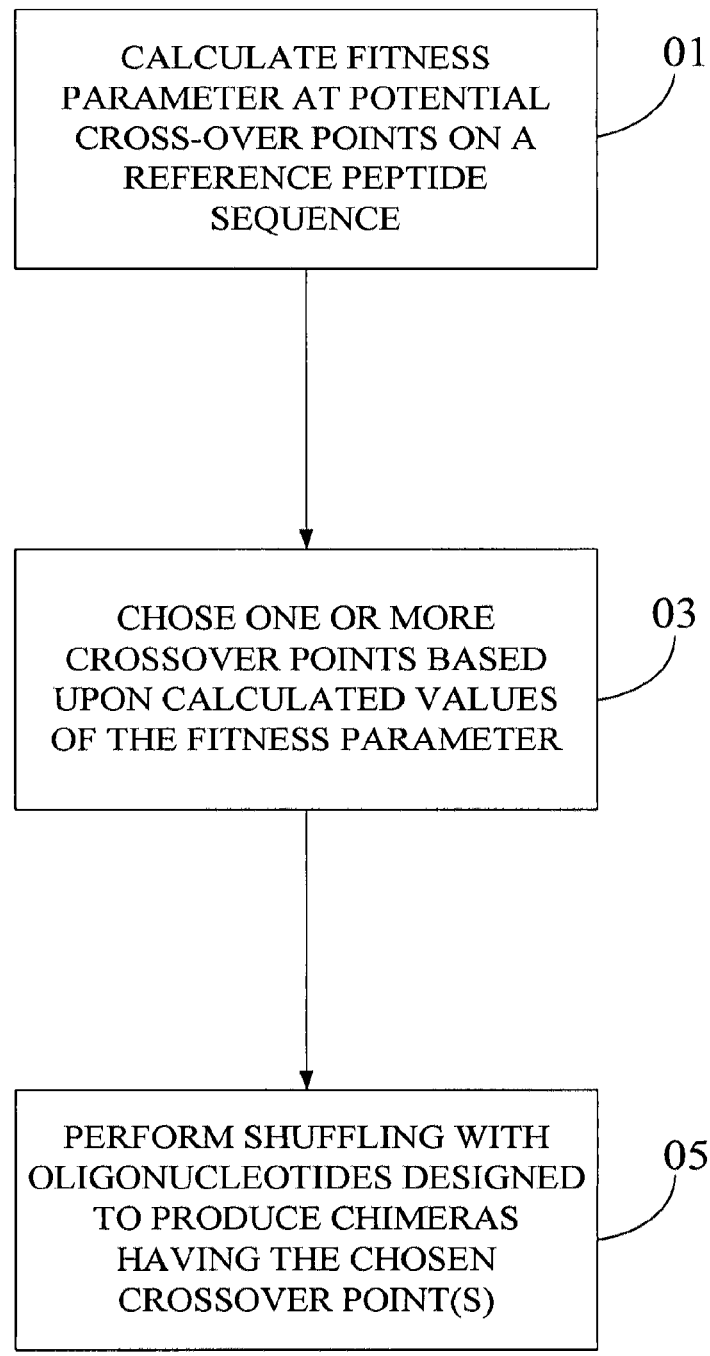

Mundorff et al., "In silico DNA Shuffling," Manuscript submitted to Nature Structural Biology, 23 Pages (1994).

Bahar et al., "Inter-residue Potentials in Globular Proteins and the Dominance of Highly Specific Hydrophilic Interactions at Close Separation," J. Mol. Biol., 266, 195-214 (1997).

Singh et al., "Application of Genetic Algorithms to Combinatorial Synthesis: A Computational Approach to Lead Identification and Lead Optimization," J. Am. Chem. Soc. 118, 1669-1676 (1996).

Skorobogatiy et al., "An Analytical Approach to Protein Design," printed from website http://www.netsci-journal.com/97v2/25.htm on Dec. 17, 2001—Abstract.

Betancourt et al., "Pair Potentials for Protein Folding: Choice of Reference States and Sensitivity of Predicted Native States to Variations in the Interaction Schemes," Protein Science, 8: 361-369 (1999).

Stemmer, WPC, "Rapid Evolution of a Protein In Vitro by DNA Shuffling", Nature, Aug. 4, 1994, vol. 370, pp. 389-391.

Jan Drenth, Principles of Protein X-Ray Crystallography, Springer-Verlag, pp. 12-18, 1995.

Robert F. Service, "Tapping DNA for Structures Produces a Trickle," News Focus, Science, vol. 298, pp. 948-950, 2002.

Accelrys Website, GCG Wisconsin Package, 15 Pages, 2002.

Lewis Ricki, The Scientist, pp. 1-4, 1993.

Chen et al., "Tuning the Activity of an Enzyme for Unusual Environments: Sequential Random Mutagenesis of Substilisin E for Catalysis in Dimethylformamide," Proc. Natl. Acad. Sci. USA, vol. 90, pp. 5618-5622, 1993.

Abkevich et al., "Impact of Local and Non-Local Interactions on Thermodynamics and Kinetics of Protein Folding," J. Mol. Biol., 252: 460-471, 1995.

Richards et al., "Advances in Protein Chemistry," Adv. Protein Chem., 55:ix-xi, 2000.

M. Ostwemeier et al., "A Combinatorial Approach to Hybrid Enzymes Independent of DNA Homology," Nature Biotechnology, vol. 17, pp. 1205-1209, 1999.

Arnold, "Combinatorial and Computational Challenges for Biocatalyst design", Nature, 2001, 409(6817):253-257.

Boder et al., "Directed Evolution of Antibody Fragments with Monovalent Femtomolar Antigen binding Affinity", Proc. Natl. Acad. Sci. USA, 2000 97(20):10701-10705.

Bohm, "New approaches in molecular structure prediction", Biophys Chem., 1996, 59: 1-32.

Chen & Arnold, F.H., "Tuning the Activity of an Enzyme for Unusual Environments: Sequential Random Mutagenesis of Subtilisin E for Catalysis in Dimethyyformamide", Proc. Natl. Acad. Sci. U.S.A. 1993, 90:5618-5622.

De Maeyer et al., "All in One: A Highly Detailed Roamer Library Improves Both Accuracy and Speed in the Modeling of Sidechains by Dead-End Elimination", Folding & Design, 1997, 2, 53-66.

Desjarlais & Clarke N.D., "Computer Search Algorithms in Protein Modification and Design," Curr. Opin. Struct. Biol., 1998, 8:471-475.

Dube et al., "Selection of New Biologically Active Molecules from Random Nucleotide Sequences," Gene 1993, 137:41-47.

Dunbrack & Karplus, M., "Backbone-Dependent Rotamer Library for Proteins Application to Sidechain Prediction," J. Mol. Biol. 1993, 230:543-574.

Dunbrack & Karplus, "Conformational Analysis of the Backbone-Dependent Roamer Preferences of Protein Sidechains," Nature Struct. Bio/. 1994, 1:334-340.

Fetrow et al ., "New program for Protein Tertiary Structure Prediction," Biotechnol., 1993, 11(4):479-484.

Flickinger et al., "Enzymes, Directed Evolution", in 2 Encyclopedia of Bioprocess Technology: Fermentation, Biocatalysis, and Bioseparation 1999, 2:971-987.

Giver et al, "Directed evolution of a Thermostable Esterase," Proc. Nat!. Acad. Sci., USA 1998, 95:12809-12813.

Godzik, "In Search of the Ideal Protein Sequence," Protein Engineering, 1995, 8:409-416.

Hogue et al., "Structure Databases," Methods Biochem. Anal. 1998, 39:46-73.

Johnson et al., "The Traveling Salesman Problem: A Case Study in Local Optimization," In Local Search in Combinatorial Optimization, Edited by Aarts et al., John Wiley & Sons Ltd., 21-310, 1997.

Geladi et al., "Partial Least Squares Regression: A Tutorial," Anal Chim Acta, 168: 1-17, 1986.

Holowachuk et al., "Efficient Gene Synthesis by Klenow Assembly/Extension-Pfu Polymerase Amplification (KAPPA) of Overlapping Olingonucleotides," PCR Methods Appl, 4:299-302, 1995.

Aita et al., "Theory of Evolutionary Molecular Engineering Through Simultaneous Accumulation of Advantageous Mutations," J. Theor. Biol., 207:543-556, 2000.

Jain et al., "The Crystal Structure of an Autoprocessed Ser221 Cys-subtilisin E-propeptide Complexat 2.0 A Resolution," Mol. Biol. 1998, 284:137-144.

Joo et al., "Laboratory Evolution of Peroxide-Mediated Cytochrome P450 Hydroxylation.," Nature 1999, 399:670-672.

Kay, "NMR Methods for the Study of Protein Structure and Dynamics," Biochem. Cell Biol., 1997, 75:1-1 5 (1997).

Koehl & Delarue, "Application of a Self-consistent Mean Field Theory to Predict Protein Side-chains Conformation and Estimate Their Conformational Entropy", J. Mol. Bioi. 1994, 239:249-275.

Koehl & Delarue, Mean-field Minimization Methods for Biological Macromolecules Curr. Opin. in Struct. Biol. 1996, 6:222-226.

Lazar, "De Novo Design of the Hydrophobic Core of Ubiquitin," Protein Science, 1997, 6: 1167-1178.

Lee & Richards, "The Interpretation of Protein Structures: Estimation of Static Accessibility," J. Mol. Biol., 1971, 55: 379-400.

Lee & Subbiah "Prediction of Protein Side-chain Conformation by Packing Optimization," J. Mol. Biol., 1991, 217,373-388.

Lee, "Predicting Protein Mutant Energetics by Self-consistent Ensemble Optimization," J. Mol. Biol., 1994, 236:918-939.

Levitt et al., "Protein folding: The endgame," Annu. Rev. Biochem., 1997, 66:549-579.

Li et al., "Emergence of Preferred Structures in a Simple Model of Protein Folding," Science 1996, 273:666-669.

Matsumura et al., "Structural Studies of Mutants of T4 Lysozyme That Alter Hydrophobic Stabilization," J. Biol. Chem. 1989, 264:16059-16066.

Miyazaki & Arnold, "Exploring Nonnatural Evolutionary Pathways by Saturation Mutagenesis: Rapid Improvement of Protein Function," J. Molecular Evolution, 1999, 49:716-720.

Miyazaki & Arnold, "Directed Evolution Study of Temperature Adaptation in a Psychrophilic Enzyme," J.Mol. Biol. 2000, 297:1015-1026.

Moore & Arnold, "Directed Evolution of a Para-nitrobenzyl esterase for aqueous-organic Solvents," Nature Biotechnology, 1996, 14(4):458.

Nikolova et al., "Semirational Design of Active Tumor Suppressor P53 DNA Binding Domain with Enhanced Stability," Proc. Natl. Acad. Sci. U.S.A. 1998, 95:14675-14680.

Pjura et al, "Development of an in vivo Method to Identify Mutants of Phage T4 lysozyme of Enhanced Thermostability," Protein Science 1993, 2:2217-2225.

Fontana & Shuster, "Continuity in Evolution: On the Nature of Transitions," Science 1998, 280:1451-1455.

Sasai, "Conformation, Energy, and Folding Ability of Selected Amino Acid Sequences," Proc. Natl. Acad. Sci. USA, 1995, 92: 8438-8442.

Saven & Wolynes, "Statistical Mechanics of the Combinatorial Synthesis and Analysis of Folding Macromolecules," J. Phys. Chem. B. 1997, 101:8375-8389.

Skandalis et a/., "Creating Novel Enzymes by Applied Molecular Evolution," Chem. Biol. 1997, 4:889-898.

Whitlow, "1.85 A structure of Anti-Fluorescein 4-4-20 Fab," Protein Engineering, 1995, 8:749-761.

Wilson et al., "Modeling Side-chain Conformation for Homologous Proteins Using an Energy-Based Rotomer Search," J. Mol. Biol. 1993, 229:996-1006.

Wuthrich, "NMR—This Other Method for Protein and Nucleic Acid Structure Determination," Acta Cyrstallogr., 1995, D51:249-270.

You & Arnold, "Directed Evolution of Subtilisin E in Bacillus subtilis to Enhance Total Activity in Aqueous Dimethylformamide", Protein Engineering 1994, 9(1):77-83.

Zhao & Arnold, "Optimization of DNA shuffling for High Fidelity Recombination," *Nuci. Acids Res.*, 1997, 25(6):1307-1308.

Zhao & Arnold, "Directed Evolution Converts Subtilisin E into a Functional Equivalent of Thermitase," *Protein Engineering 1999*, 12(1):47-53.

Martin et al., "Measuring Diversity: Experimental Design of Combinatorial Libraries for Drug Discovery," J. Med. Chem. 38, 1431-1436, 1995.

Sheridan et al., "Using a Genetic Algorithm to Suggest Combinatorial Libraries," J. Chem. Inf. Compu. Sci., 35, 310-320, 1995.

D.K. Agrafiotis, "Multiobjective Optimization of Combinatorial Libraries," IBM J. Res & Dev., vol. 45, No. 3, 545-566, 2001.

Peter Balling, "Is Random Mutation More Rational", Nature Biotechnology, vol. 14, Apr. 1996.

Jonathan King, "Unexpected Pathways to Protein Stabilization", Nature Biotechnology, vol. 14, Apr. 1996.

Roger Sheldon, "Picking a Winner", Nature, vol. 399, Jun. 17, 1999, pp. 636-637.

Holler et al., "In Vitro evolution of a T Cell Receptor with High Affinity for Peptide/MHC", Proc. National Academy Sci. USA, vol. 97, No. 10, May 9, 2000, pp. 5387-5392.

Foote et al., Breaking the Affinity Ceiling for Antibodies and T. Cell Receptors, Proc. National Academy Sci. USA, vol. 97, No. 20, Sep. 26, 2000, pp. 10679-10681.

U.S. Office Action mailed Mar. 13, 2006, from U.S. Appl. No. 10/379,378.

U.S. Office Action mailed Sep. 28, 2006, from U.S. Appl. No. 10/379,378.

Ivanisenko et al., "Search for Sites with Functionally Important Substitutions in Sets of Related or Mutant Protein," Biopolymer Physics and Physical Chemistry, Molecular Biology, vol. 31, No. 5, 1997, pp. 749-755.

Eroshkin et al., "Proanal version 2: multifunctional program for analysis of multiple protein sequence alignments and for studying the structure-activity relationships in protein families," CABIOS, vol. 11, No. 1, 1995, pp. 39-44.

Eroshkin et al., "Algorithm and computer program Pro_Anal for analysis of relationship between structure and activity in a family of proteins or peptides," CABIOS, vol. 9, No. 5, 1993, pp. 491-497.

European Search Report dated Oct. 12, 2006 from related European Application No. 03711540.9-2201 PCT/US0307610.

U.S. Examiner Interview Summary dated Mar. 24, 2008 issued in U.S. Appl. No. 10/386,903.

U.S. Examiner Interview Summary dated May 9, 2008 issued in U.S. Appl. No. 10/386,903.

U.S. Examiner Interview Summary dated Dec. 3, 2008 issued in U.S. Appl. No. 10/386,903.

U.S. Office Action dated Apr. 25, 2011 issued in U.S. Appl. No. 11/818,237.

PCT International Search Report dated Dec. 18, 2003 issued in PCT/US2003/007610.

PCT International Preliminary Examination Report dated Nov. 1, 2004 issued in PCT/US2003/007610.

European Office Action dated Jan. 24, 2007 issued in EP 03 711 540.9-1225.

European Office Action dated Jul. 16, 2010 issued in EP 03 711 540.9-1225.

Japanese Final Office Action dated Feb. 1, 2011 issued in JP 2003-576577.

A.M. ter Laak, et al., "Modelling and mutation studies on the histamine $H_1$-receptor agonist binding site reveal different binding modes for $H_1$-agonists: $Asp^{116}$ (TM3) has a constitutive role in receptor stimulation," Journal of Computer Aided Molecular Design, vol. 9, 1995, pp. 319-330.

Dandekar, et al., "Applying experimental data to protein fold prediction with genetic algorithm," Protein Engineering, vol. 10, 1997, pp. 877-893.

Office Action mailed Jan. 27, 2006, from U.S. Appl. No. 10/386,903.
Office Action mailed Aug. 11, 2006, from U.S. Appl. No. 10/386,903.
Final Office Action mailed Jan. 25, 2007, from U.S. Appl. No. 10/386,903.
Office Action mailed Jul. 30, 2007, from U.S. Appl. No. 10/386,903.
Office Action mailed Jul. 24, 2008, from U.S. Appl. No. 10/386,903.
Final Office Action mailed Apr. 15, 2009, from U.S. Appl. No. 10/386,903.
Notice of Allowance mailed Jul. 15, 2009, from U.S. Appl. No. 10/386,903.
Allowed Claims for U.S. Appl. No. 10/386,903, Mailed Jul. 15, 2009.
Japanese Office Action mailed May 26, 2009, from Application No. 2003-576577.

U.S. Appl. No. 12/557,434, Notice of Allowance mailed Dec. 7, 2011.

U.S. Appl. No. 12/557,434, Allowed Claims, Dec. 7, 2011.

JP patent application No. 2009-188786, Office Action mailed Mar. 21, 2012.

* cited by examiner

OPTIMIZATION OF CROSSOVER POINTS FOR DIRECTED EVOLUTION

CROSS-REFERENCE TO RELATED APPLICATIONS

This application is a divisional of and claims priority under 35 U.S.C. §120 from U.S. Ser. No. 10/386,903, filed Mar. 10, 2003, now U.S. Pat. No. 7,620,500 which claims benefit under 35 U.S.C. §119(e) of U.S. Ser. No. 60/363,505, filed Mar. 9, 2002 and of U.S. Ser. No. 60/373,591, filed Apr. 18, 2002. These applications are incorporated herein in their entireties for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention is in the field of bioinformatics and structure-activity relationships (SAR), and the application of structure-activity analyses to the process of recombinant protein and nucleic acid design.

BACKGROUND OF THE INVENTION

The search for new or improved function of biological molecules is a challenging endeavor. Methods for generating and screening libraries of variant proteins have been developed, e.g., to make and identify proteins exhibiting a desired property (see, for example, Stemmer, W. P. (1994) "Rapid evolution of a protein in vitro by DNA shuffling" *Nature* 370:389-391). Some methods result in the generation of a library containing few functional molecules (see, for example, Ostermeier (1999) "A combinatorial approach to hybrid enzymes independent of DNA homology" *Nature Biotech* 17:1205). Limitations in screening capacity can make it difficult to find such functional molecules. Accordingly, a need exists for methods of producing libraries of biomolecules that are enriched for functional biomolecules.

SUMMARY OF THE INVENTION

The present invention provides methods and devices for more efficiently engineering diversity into recombinant polypeptides and/or nucleic acids. For example, a variety of methods of selecting and/or assessing potential recombination crossover sites in an amino acid sequence or a nucleotide sequence are provided, as well as the resulting chimeric product sequences. These methods include, e.g., consideration of structural, functional and/or statistical data in the selection and assessment of sequences and crossover sites for use in recombination.

More specifically, the present invention provides methods of selecting crossover points between two or more biomolecules. One aspect of the invention provides methods of determining the fitness of multiple potential crossover points on a reference peptide sequence. Such methods may be described by the following sequence of operations: (a) for each of the multiple potential crossover points on the reference peptide sequence, calculating an overall value of a fitness parameter; and (b) based on the respective overall values of the fitness parameter for the potential crossover points, choosing an actual crossover point for a chimeric peptide. This chimeric peptide includes a partial sequence from the reference sequence. In these methods, the overall value of the fitness parameter is calculated from multiple individual values of the fitness parameter for multiple chimeras having the potential crossover point under consideration. These chimeras may be generated by inserting subsequences of various lengths in the reference sequence, with each subsequence terminating at the crossover point under consideration.

After choosing an actual crossover point, the method may continue by producing at least one chimeric nucleic acid encoding the chimeric peptide. And such chimeric nucleic acid may be produced by recombining oligonucleotides, including at least one oligonucleotide encoding the chosen crossover point. This oligonucleotide includes two partial sequences, one encoding a partial sequence of one parent peptide and another encoding a partial sequence of another parent peptide, with the two partial sequences meeting at a location in the oligonucleotide corresponding to the chosen crossover point.

The fitness parameter may be any measure of the ability of a peptide to meet particular physical criteria. In one example, the fitness parameter provides a measure of a chimeric allele's ability to increase or decrease the binding specificity of a peptide. In another example, it provides a measure of a chimeric allele's ability to preserve or improve the folding of the polypeptide.

The individual values of the fitness parameter (for particular chimera sequences having the potential crossover point under consideration) may be obtained by various techniques. In one example, the individual values are calculated by the following method: (i) aligning the chimera sequence to the reference peptide sequence; (ii) identifying contacting residues of the chimera from a contact map; and (iii) summing residue-residue potentials for contacting residues of the chimera.

The reference peptide sequence may be chosen for many reasons. In one example, the reference peptide is a naturally occurring peptide. In another example, it is a non-natural peptide identified by a recombination or mutagenesis procedure. In some cases, one of the parent peptides used in the above method is itself the reference peptide sequence.

Typically, the methods will involve choosing multiple crossover points to create multiple chimeric peptides comprising partial sequences of the reference peptide. These multiple chimeric peptides may be generated as a library of peptides as described in further detail herein. Members of this library may be generated by various techniques. The present invention also provides a method of producing a selected member of the library of peptides by (i) providing an expression system from which a selected member of the library of peptides can be expressed; (ii) cloning a polynucleotide encoding the selected member of the library of peptides into the expression system; and (iii) expressing the selected member of the library of peptides.

Another aspect of the invention provides methods that include, but are not limited to, i) providing a reference sequence of a reference biomolecule or biomolecular structure; ii) generating a contact map for the reference sequence; iii) providing a first sequence of a first biomolecule and a second sequence of a second biomolecule, between which one or more crossover points are to be determined; iv) aligning the first and second sequences with the reference sequence; v) replacing a subsequence from the first sequence with a subsequence from the second sequence to produce a chimeric biomolecule sequence; vi) comparing the chimeric biomolecule sequence with the contact map to select two or more elements (e.g., nucleotide bases or amino acid sidechains or alpha carbons) in the chimeric biomolecule sequence that correspond to proximal elements in the contact map of the reference biomolecule; and vii) scoring the selected elements, wherein the score provides a measure of the likelihood of the chimeric biomolecule sequence having a stability or activity similar or identical to the reference biomolecule. Optionally, two or more subsequences are swapped during generation of the chimeric product sequence; the multiple swapped sequences can be derived from one parental sequence or from multiple (two or more) parental sequences. In one embodiment, the biomolecules are proteins or polypeptides; in another embodiment, the biomolecules being analyzed comprise nucleic acids, for example, catalytic RNA molecules or other functionally active nucleic acid molecules. The contact maps for the reference biomolecular sequence can be generated from a number of sources of data, including, but not limited to, crystallographic models, NMR data, protein folding algorithms, homology modeling, nucleotide modeling algorithms, and the like. After insertion or "swapping" of one or more regions of the parental sequences, selected elements of the resulting chimeric molecule(s) are compared to comparably positioned elements in the reference molecule; the scoring of these selected elements provides a mechanism for assessing the crossover sites employed in the in silico recombination procedure.

In another aspect, the present invention also provides a computer or computer-readable medium with instructions for, for example, assessing crossover points or predicting recombination outcomes. The computer or computer-readable medium includes a computer code that i) inputs a reference sequence of a reference biomolecule; ii) generates a contact map for the reference sequence; iii) aligns a first sequence and a second sequence with the reference sequence; iv) replaces a subsequence in the first sequence with a subsequence in the second sequence to produce a chimeric sequence; v) compares the chimeric sequence with the contact map to select two or more elements in the chimeric amino acid sequence that correspond to proximal elements in the contact map; and vi) scores the selected elements, wherein the score (and thereby the computer readable medium) provides a measure of the likelihood that the chimeric sequence retains some semblance of the tertiary structure or a similar activity as compared to the reference sequence, thereby assessing crossover points or predicting recombination outcomes of a selected recombination event.

The amino acid spacing of a reference protein can be determined by a number of techniques known to one of skill in the art, including, for example, crystallography, NMR spectroscopy, EPR spectroscopy, and the like. Alternatively, the information may be publicly available, or generated in silico; software for performing protein folding analyses or molecular modeling and/or calculating inter-residue distances is available from several vendors and can be used to identify amino acid residues within a critical distance of each other. The critical distance can vary with the amino acid residues involved, the nature of the molecular interaction, and the role that the residues play with respect to the activity of the reference protein. Optionally, the critical distance ranges from about 2 Angstroms to about 6.5 Angstroms, or, e.g., about 2.5 Angstroms to about 4.5 Angstroms, or less than about 4.5 Angstroms.

In the methods and computer-based devices of the present invention, a region of a first parental sequence (e.g., an amino acid sequence) is inserted into or substituted for a region in a second parental sequence, thereby generating a chimeric, or swapped, product sequence. In some embodiments of the present invention, the reference sequence is employed as one of the parent sequences. In other embodiments, two or more "non-reference" parent sequences are assessed for recombination potential. Optionally, the first and second parental sequences have low sequence identity with one another. For the analysis, either all possible chimeric products, or a subset of the possible products, are examined for crossover potential.

Yet another aspect of the invention pertains to apparatus and computer program products including machine-readable media on which are provided program instructions and/or arrangements of data for implementing the methods and software systems described above. Frequently, the program instructions are provided as code for performing certain method operations. Data, if employed to implement features of this invention, may be provided as data structures, database tables, data objects, or other appropriate arrangements of specified information. Any of the methods or systems of this invention may be represented, in whole or in part, as such program instructions and/or data provided on machine-readable media.

These and other features of the present invention will be described in more detail below in the detailed description of the invention and in conjunction with the following figures.

BRIEF DESCRIPTION OF THE DRAWINGS

FIGS. 1A-1C present process flow diagrams depicting one embodiment of the invention.

FIG. 2, panel A, provides a map of the contact energy for every possible 2-crossover chimera of MLE I and MLE II from *P. putida* in which portions of the MLEII sequence replace segments of the reference protein MLE I. The ordinate shows the residue position in MLE I where the replacement begins, and the abscissa shows the length of the replacement. The $\Delta E_C$ is indicated by the color in the map. Chimeras that are predicted to be structurally disruptive are shown in magenta, those that are predicted to be favorable are shown in red, and neutral changes are indicated by blue and green. Panel B indicates the average $\Delta E_C$ for the 1-80 amino acid segments from *P. putida* MLE II replacing the corresponding segment of reference protein *P. putida* MLE I. The labeled positions (98, 119, 144, 172, 201, 228, 254, 280, 302, and 328) represent the amino acid numbers along the linear sequence where crossovers were designed.

DETAILED DESCRIPTION

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a nucleic acid sequence" includes a combination of two or more such sequences, reference to "a polypeptide" includes mixtures of polypeptides, and the like.

Unless otherwise defined herein, all technical and scientific terms used herein have the same meaning as commonly understood by those of ordinary skill in the art to which the present invention belongs. Although any methods and materials similar or equivalent to those described herein can be used in the practice for testing of the present invention, the preferred materials and methods are described herein.

DEFINITIONS

In describing and claiming the present invention, the following terminology will be used in accordance with the definitions set out below.

A "subsequence" or "fragment" is any portion of an entire sequence of nucleotides or amino acids. The terms "sequence" and "character strings" are used interchangeably herein to refer to the order and identity of amino acid residues in a protein (i.e., a protein sequence or protein character string) or to the order and identity of nucleotides in a nucleic acid (i.e., a nucleic acid sequence or nucleic acid character string).

The term "crossover point" as used herein refers to a position in a sequence at which the origin of that portion of the sequence changes, or "crosses over" from one source to another (e.g., a terminus of a subsequence involved in an exchange between parental sequences).

As used herein, the term "contact map" refers to a depiction of interactions between component elements of a biomolecule, typically in the form of a two-dimensional graph or data matrix, thereby providing a simplified or reduced representation of a three-dimensional structure of the biomolecule.

As used herein, the term "chimeric" is used to refer to a product of a recombination event between one or more parental molecules.

The term "proximal elements" as used herein refers to sequence components (for example, amino acid sidechains or alpha carbons, or nucleic acid bases) which are proximal, or situated close in space, to one another in a three-dimensional structure or model.

The terms "polypeptide," "peptide," and "protein" are used interchangeably herein to refer to a polymer of amino acid residues. The terms apply to amino acid polymers in which one or more amino acid residues are analogs, derivatives or mimetics of corresponding naturally occurring amino acids, as well as to naturally occurring amino acid polymers. For example, polypeptides can be modified or derivatized, e.g., by the addition of carbohydrate residues to form glycoproteins. The terms "polypeptide," "peptide," and "protein" include glycoproteins, as well as non-glycoproteins.

As used herein, the term "about" refers to a range that is optionally +/−25%, preferably, +/−10%, more preferably +/−5%, or more preferably +/−1% of a value with which the term is associated.

The present invention provides methods for selecting potential crossover sites for recombination and assessing the effect that the recombination will have upon the tertiary structure (and therefore the activity or stability) of the chimeric product. This approach permits more efficient generation of libraries of recombined sequences that are likely to provide appropriately folded products and/or desired functionalities.

Overview of Methodology

In one embodiment, the invention may be viewed as a general process employing two or more of the three operations depicted as a flow chart in FIG. 1A. As depicted in that figure, the general process begins at a block 01 with calculation of a fitness parameter as a function of various potential crossover points on a reference peptide sequence. The fitness parameter may be calculated as a change in fitness with respect to the reference sequence when substituting one or more amino acids from the reference sequence with corresponding amino acids from a different sequence—to produce the crossover point. When the operation of block 01 is completed, one has a separate calculated fitness value for each of a series of potential crossover points (identified before or after particular residue positions in the peptide sequence). Block 03 in the flow chart shows that one or more specific crossover points are then chosen from among all the potential crossover points based upon the values of the fitness parameters. Crossover points where the fitness parameters appear to be maximized (or at least meet a particular threshold) are chosen for subsequent synthesis by, for example, recombination procedures. Using these crossover points increases the likelihood that the chimeric peptides will be "fit" for an intended purpose.

As indicated at block 05 of FIG. 1A, the method next involves producing chimeric peptides having one or more of the chosen crossover points. These peptides may comprise a library, the members of which can be produced by various procedures. One suitable procedure involves synthesizing full-length chimeric nucleic acid libraries by recombining oligonucleotides, including some designed to produce chimeras having the chosen crossover points. This may be accomplished by employing oligonucleotides having two partial sequences, one from one parent and another from another parent, with the two partial sequences meeting at the crossover point defined on the reference sequence. Note that while the first two operations in FIG. 1A involve data manipulation, the last operation involves a physical procedure. Stated another way, only those protein variants which pass a computational pre-screen (based on crossover point fitness) are then generated in the laboratory by, for example, synthesizing polynucleotides encoding the protein variants, followed by expression of the polynucleotides. One could also use these techniques to create a library enriched for functional variants; i.e., not a library that contained only these predicted better variants, but one that contained mostly these predicted variants.

In some cases, the fitness parameter or change in fitness parameter calculated in block 01 of FIG. 1A is a measure of the polypeptide's stability. Examples of polypeptide fitness parameters include measures of a chimeric allele's ability to (1) preserve or improve the folding of the polypeptide and (2) increase or decrease the binding specificity of the polypeptide as desired.

To explore the "crossover space" of the reference peptide sequence (block 01 of FIG. 1A), the algorithm calculates the fitness at each potential crossover point (identified before or after particular residue positions in the peptide sequence) of the reference sequence. The reference sequence itself may be the sequence of a naturally occurring peptide or of an unnatural peptide such as one identified by recombination or other directed evolution technique. Further, the reference sequence may be one parent sequence chosen for use in a subsequent recombination procedure. Or it may be a sequence that is not itself used in a recombination procedure. Either way, it is preferably related to one or more of the other parent sequences employed in the subsequent recombination procedure. As described elsewhere herein, the reference sequence and the one or more parental sequences employed in a recombination procedure can be related as members of a protein family.

Figure 1B:
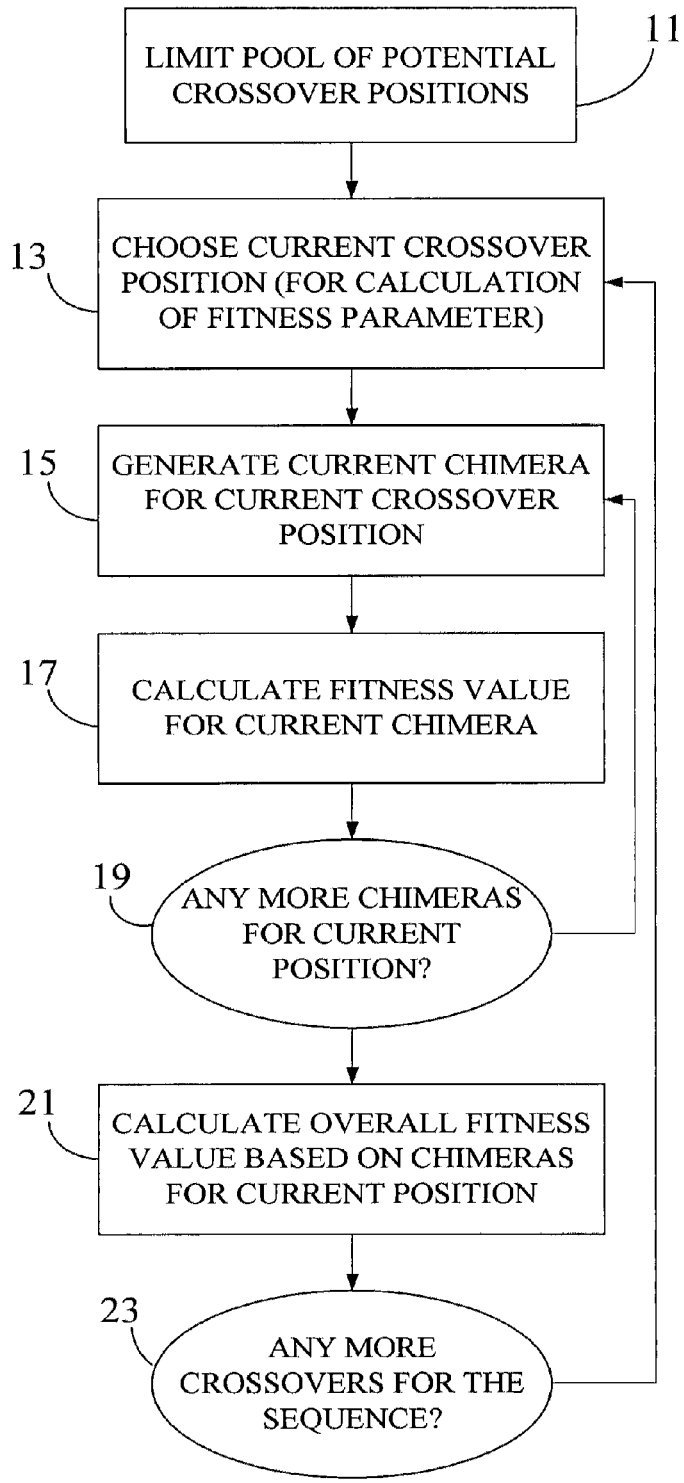

FIG. 1B depicts one exemplary procedure for implementing block 01 of FIG. 1A. The process begins at a block 11 with the algorithm optionally limiting the pool of potential crossover positions in the reference sequence to a subset for which the fitness value will be calculated. In one example, potential crossover positions are limited to every fifth residue or some other regular position. Or potential crossover positions are limited to residues in particular secondary or tertiary structures such as loop regions of a solved structure of the reference peptide.

Next, at a block 13, the algorithm identifies a "current" crossover position in the reference sequence. Note that the algorithm may simply march along the sequence starting at the N or C terminus of that sequence, and consider one potential crossover point after another. Or it may employ some other order in evaluating potential crossover positions. Regardless of the order in which the algorithm selects crossover positions for consideration, those individual crossover points are considered separately. During consideration, a crossover point becomes the "current" crossover position for purposes of the algorithm. (This does not exclude the possibility that multiple crossover points could be considered concurrently in a parallel processing implementation, for example.)

With the "current" crossover position set, the algorithm next generates a "current" chimera for that position. See block 15. Understand that certain preferred embodiments of the invention consider numerous chimeras having the same crossover point (as defined in the reference sequence) to obtain an "overall" fitness parameter at that crossover point. For each of these chimeras, the fitness parameter is individually calculated. These numerous fitness values are then combined or otherwise considered together in arriving at the overall fitness parameter for the particular crossover position in the reference sequence. Thus, it is often necessary to evaluate multiple chimeras for a given crossover point.

With this explanation, it follows that the next successive block in the algorithm of FIG. 1B (block 17) involves calculation of the fitness value for the current chimera. And after that value has been calculated, the algorithm determines whether there are any more chimeras to be considered for the current crossover position of the reference sequence. See block 19. If more chimeras remain to be considered, process control returns to block 15 where a next current chimera is considered for the current crossover position. Before this takes place, the calculated fitness value for the previous chimera is stored independently or possibly combined with a running overall fitness value that is successively updated with each chimera considered at the crossover position.

Assuming that there are no more chimeras to consider at the current crossover position (block 19 returns a "No"), the algorithm next calculates an overall fitness value based on all the chimeras for the current position. See block 21. Again, the overall fitness value represents a value that takes into consideration each of the fitness values for the individual chimeras at the crossover position. That overall value is made available to compare the current potential crossover position with other potential crossover positions on the reference sequence. If the fitness value for the crossover position compares favorably with its peers, it may be chosen as a crossover position for a subsequent recombination process.

After the overall fitness value has been calculated for a particular crossover position, the algorithm next determines whether there are any more potential crossover positions to be considered in the reference sequence. See block 23. If so, process control returns to block 13 where the next potential crossover position is selected for analysis and an overall fitness value is generated for that position. If not, the process of block 01 in FIG. 1A is complete. In the depicted example, process control would then transfer to block 03 of FIG. 1A, where one or more of the crossover points in the reference sequence is selected based upon relative overall values of the fitness parameter.

Figure 1C:
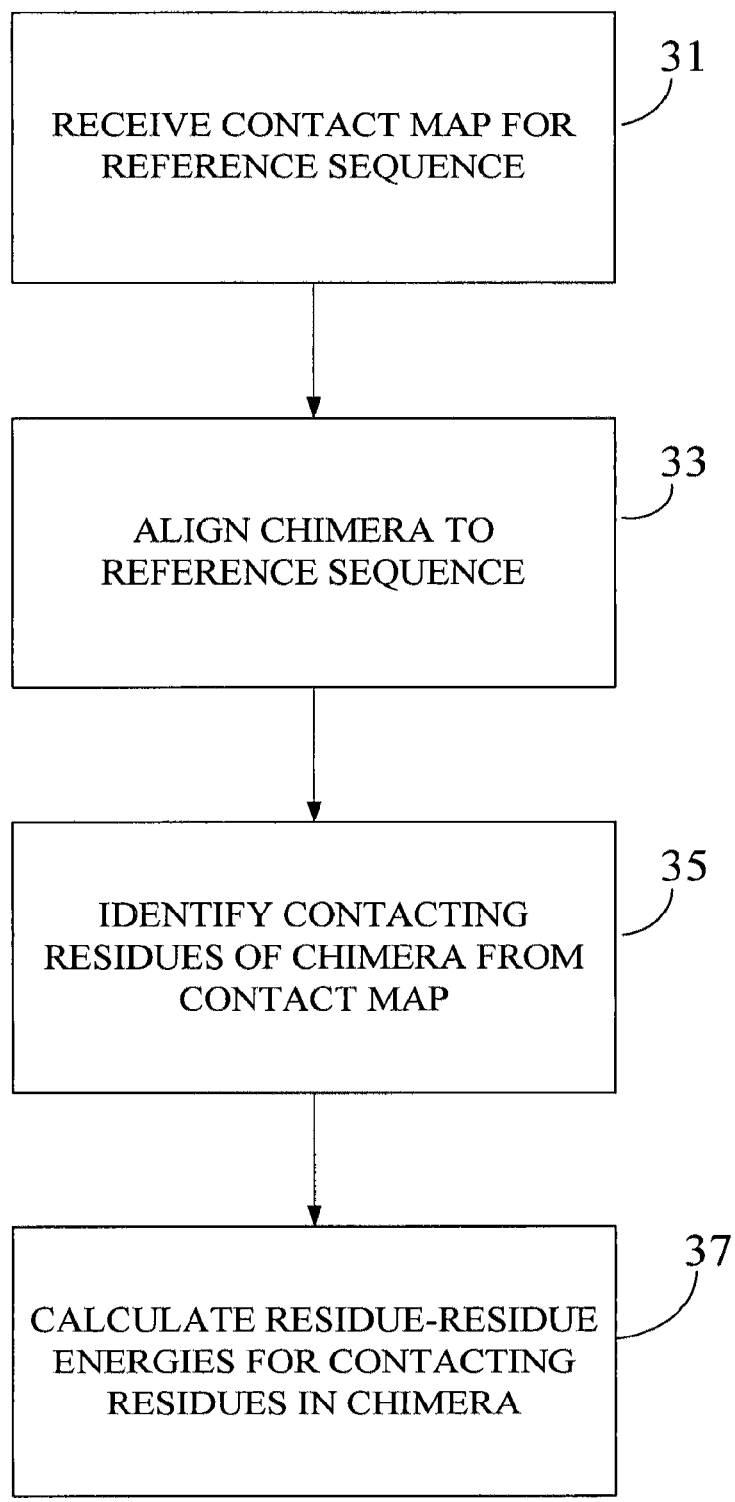

The algorithm may employ a substitution in which one more subsequences from the reference sequence are replaced with one or more corresponding subsequences from a different (albeit related) sequence. In all cases, the resulting chimera should have a crossover between the reference sequence and the other sequence at the position currently under consideration in the algorithm. In block 17 in FIG. 1B, the actual calculation employed depends upon the particular fitness parameter employed. In one preferred embodiment, the fitness parameter is a contact energy. Contact energy is a measure of the stability of a polypeptide. It may be calculated by summing residue-residue potentials of pairs of contacting residues in the polypeptide. One specific process for calculating contact energy is depicted in FIG. 1C. As shown there, the process begins at block 31 with receipt of a "contact map" for the reference sequence (or potentially some other related sequence). Then at block 33, the algorithm aligns the current chimera to the reference sequence. This allows the residues of the chimera to be positioned properly in the contact map, and thereby reflect the likely folding of the chimera. Thus, at block 35, the algorithm applies the contact map to the aligned chimera. Finally at 37, the procedure calculates residue-residue energies for "contacting" residues in the chimera. The contacting residues were identified by their positions in the contact map.

Generally, a contact map identifies those residues of a polypeptide or other polymer that are sufficiently proximate to one another that they are deemed to interact with one another in some defined way. Such proximate residues are said to be in "contact" with one another. Two residues are sufficiently proximate to be in contact if they are separated by no more than a defined separation distance. Typically, the interaction in question is an energetic or steric interaction between at least two residues. In some implementations, different interactions have different separation distances. For example, in one embodiment, two residues separated by no more than about 4.5 angstroms are deemed to be in contact for hydrogen bonding, ionic bonding, and/or hydrophobic interaction, while two cysteine residues separated by no more than about 2.5 angstroms are deemed to be in contact for disulfide interaction. Generally, a contact map provides a convenient way to identify residues that contribute to some property of the polypeptide such as the stability of a particular folding arrangement. Every pair of residues in a polypeptide interacts to some degree and can therefore contribute to the property of interest. However, only those residue pairs separated by less than very limited distances contribute significantly.

Hence, a contact map can place a reasonable limit on the number of residue combinations used to calculate the property. In this way, the computational work required for the calculation is minimized without sacrificing significant accuracy. Basically, only the contacting residue pairs identified with the contact map are used in calculations of the property for the overall polypeptide. Other, non-contacting residues are not included in the calculations because alteration of the non-contacting residue side-chains is less likely to disrupt specific interactions within the protein and therefore less likely to cause significant structural disruption.

In one example, the contact map is simply a three-dimensional representation of the arrangement of residues in a polypeptide. Such arrangement may represent residue positions deduced by solving the polypeptide's structure using x-ray diffraction data for example. The contacting residues in the polypeptide are identified by their separation distances as described above.

Of importance to this invention, a contact map derived from the three-dimensional structure of a reference polypeptide sequence can be used for one or more related polypeptide sequences (typically chimeras having the crossover points under consideration). A related sequence is aligned with the reference polypeptide sequence and then arranged in the contact map in a manner preserving the alignment. The residues of related sequence are assumed to occupy the same locations as the corresponding residues of the reference sequence. From this arrangement, contacting residues are identified for the related sequence.

In one preferred embodiment, the contact potentials for any two residues are calculated by the Miyazawa and Jernigan potentials. These are described in the various references cited elsewhere herein. Basically, the "M-J potentials" of contacting residues are summed over the entire polypeptide. The resulting sum gives an overall measure of the chimera's stability. Note that the chimera folding is presumed to match that of the reference sequence from which the contact map was derived. The residue-residue potentials are calculated by taking into consideration solvent effects. They also take into consideration the type of residue and the secondary structure at the residue.

As indicated in the above discussion, to estimate the effect of a substitution at any potential crossover point on a reference polypeptide, one or more chimeras may be generated having the crossover point in question. See block 15 of FIG. 1B. In the simplest embodiment only a single chimera is generated having the selected crossover point. In this simple embodiment, the contact energy of that chimera is compared with the contact energy of the reference sequence to get a change in contact energy ($\Delta E_c$ of FIG. 1B).

In a more typical scenario, the change in contact energy at potential crossover points is obtained by averaging the change calculated for many different chimeras—each having the crossover point in question. The various chimeric sequences having a particular crossover point and used to calculate the fitness parameter can be chosen to meet particular criteria. In one embodiment, multiple subsequences to the N and/or C sides of the crossover point are chosen for substitution in the reference sequence. These subsequences may be taken from other "parental" sequences related to the gene encoding the reference sequence. The subsequences can be systematically selected from another parental sequence. For example, one subsequence to the N side of the crossover point can have a single residue, another can have two residues, a third can have three residues, etc. The same systematic set of substitutional subsequences can be obtained on the C side of the crossover point.

In a specific example, the chimeras associated with any given crossover point include 1 through 80 residue subsequences taken from the C side of the crossover point in a second parental sequence and 1 through 80 residue subsequences taken from the N side of the crossover point. These subsequences are substituted in a first parental sequence at the corresponding locations in that sequence. Hence 160 different chimeras are generated to calculate the importance of a particular crossover point—assuming that the crossover point is at least 80 residues removed from the C and N terminuses of the first parental polypeptide. Each of these chimeras has its own $\Delta E_c$. The average $\Delta E_c$ of each of these individual chimera $\Delta E_c$'s is used to reflect the overall resistance of the crossover point to unfavorable substitutions.

As suggested by this approach, some embodiments of the invention are intended to design libraries of chimeras in which crossover positions are selected based on the likelihood that they will work well as one of multiple crossovers, rather than as a single crossover. In this approach, the average contact energy is calculated for multiple insertion segments associated with a given crossover position.

Reference Sequences

In one embodiment, the methods of the present invention include providing a reference sequence of a reference biomolecule or biomolecular structure. In another embodiment, the methods include providing a reference sequence and a tertiary structure of a reference biomolecule, wherein the reference sequence comprises a plurality of elements such as monomer units (e.g., amino acids or nucleotides). Both of these approaches involve providing a reference sequence for comparison purposes. Optionally, one of the parent sequences can be employed as the reference sequence. The reference sequence is composed of a plurality of elements, such as nucleotides or amino acids, and has a defined (or determined) tertiary structure. The reference sequence can be provided in a number of ways known to one of skill in the art. For example, either an amino acid sequence of a reference protein or a nucleic acid sequence encoding the reference protein can be provided. The nucleic acid sequence encoding the protein can be provided in any of a number of formats, including, but not limited to, cDNA, mRNA, genomic DNA and the like.

In one embodiment of the present invention, the reference amino acid sequence is provided by sequencing the reference protein. Amino acid sequencing techniques are known to one of skill in the art (e.g., methods using 2,4-dinitrofluorobenzene (Sanger's reagent), dansyl chloride, phenylisothiocyanate (Edam degradation procedure), various proteases, and the like).

More commonly, the reference sequence is provided by sequencing the nucleic acid encoding a reference protein (or a catalytic oligonucleotide). Nucleic acid sequencing techniques are also known to one of skill in the art, and include, but are not limited to, the techniques set forth in Berger and Kimmel, *Guide to Molecular Cloning Techniques Methods in Enzymology* volume 152 Academic Press, Inc., San Diego, Calif. ("Berger"); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel").

In yet another embodiment of the present invention, the reference sequence is supplied by providing a nucleic acid sequence and either translating the provided nucleic acid sequence into an amino acid sequence, or transcribing the sequence to generate an oligonucleotide sequence. Optionally, the reference sequence is provided by querying a nucleic acid or protein database. Both public and commercial databases are available, such as the GenBank® databases from the National Center for Biotechnology Information (www.ncbi.nlm.nih.gov), the NCBI EST sequence database, the EMBL Nucleotide Sequence Database, Incyte's (Palo Alto, Calif.) LifeSeq™ database, and Celera's (Rockville, Md.) "Discovery System"™ database), the PROSITE databases administered by the ExPASy (Expert Protein Analysis System) proteomics server of the Swiss Institute of Bioinformatics (http://us.expasy.org), other Internet listings, and the like.

A number of protein families can be assessed for recombination potential using the methods of the present invention. Exemplary proteins and protein families include, but are not limited to, the enolase superfamily, the N-acetylneuraminate lyase superfamily, the crotonase superfamily, and members of the vicinal oxygen chelate fold (see, for example, Babbitt, P C and Gerlt, J A (1997) "Understanding Enzyme Superfamilies." *J. Biol. Chem.* 272: 30591-30594). Additional target protein families are discussed in the references cited herein (and incorporated by reference). One superfamily of particular interest is the muconate lactonizing enzymes (muconate cycloisomerases) involved in aromatic compound metabolism. Superfamily members typically share a common structural fold and utilize a similar mechanistic strategy. Thus, even at low parental sequence identity, chimeras can be generated that retain the necessary structural fold and basic mechanistic elements but yet have additional desired properties.

In addition, functionally active nucleic acid molecules, or other nucleic acid sequences of interest, can be assessed for recombination potential. For example, catalytic RNA molecules can be subjected to recombination or other diversity generating procedures, thereby modifying their substrate specificity, catalytic rates, or the like, and as such provide additional target biomolecules for use in the present invention. As another example, mRNA, rRNA or tRNA molecules can be examined using the methods of the present invention and used to generate oligonucleotides with differing activities or susceptibilities. Additional functionally-active nucleic acids include, but are not limited to, RNA and/or DNA molecules acting as biological substrates or cofactors in, for example, a protein-catalyzed reaction.

The methods of the present invention can be employed to assess crossover points among any number of additional target biomolecules or biopolymers. Additional exemplary biopolymers include, but are not limited to, carbohydrates, polyketides, terpenoids, nonribosomal peptides, lipids, or any other biopolymer that forms a stable 3D structure, e.g., in solution.

Contact Maps

The methods of the present invention involve a comparison of one or more parameters describing the tertiary structure of the reference biomolecule to the predicted parameters or structure of one or more chimeric recombination products. These parameters are provided in the form of a "contact map," wherein the interactions among component elements of the biomolecule being mapped are depicted (typically in the form of a two-dimensional graph or data matrix), thereby providing a simplified or reduced representation of the three-dimensional structure of the biomolecule. While pairwise interactions between proximal biomolecule components are typically examined, interactions among three or more proximal elements can also be employed in the contact maps of the present invention.

In certain embodiments of the methods of the present invention, a contact map is generated for the elements in the reference sequence. Typically the primary sequence of the reference molecule and any available tertiary structural data are used to generate the contact map. The contact map delineates, for example, pairs or sets of amino acid residues which are proximal or adjacent to one another in the 3-dimensional structure of the reference protein (e.g., contact amino acids). Optionally, the contact map includes data reflecting the distances between proximal elements of interest. In one embodiment of the present invention, the contact map includes scores weighted by the distance between contact amino acids. In another embodiment, the contact map comprises scores weighted by the position of the element (e.g., amino acid or nucleotide) in the reference biomolecule.

Contact maps can be generated by methods known to one of skill in the art based upon data from a variety of sources. For example, X-ray crystallographic data is commonly used to determine amino acid spacing within a protein structure and to identify amino acid residues within a critical distance of each other (e.g. proximal residues). These methods can also identify one or more physical characteristics of the interaction, including, but not limited to, the type of amino acid interaction (hydrophobic, hydrogen-bonding, and/or ionic), one or more of which can be weighted separately in the summation of the contact energy. Crystallographic data can also optionally be used to generate a "temperature factor" for each atomic position. The data provides an indication of how well-defined the contacting residues are; the contacts can then be weighted accordingly.

Alternatively, the spacing among component elements can be determined from an NMR model of the reference biomolecule. NMR experiments such as 2D-COSY and NOESY can both identify elements proximal to one another in the three-dimensional structure, as well as provide an estimate of the distance between them. The resulting contacts can then be weighted by the degree of uncertainty in the NMR models.

Furthermore, a contact map can be generated for a reference protein using amino acid configurations and distances based upon protein-folding analysis or homology modeling of the reference protein. Software for performing protein folding analyses, for calculating inter-residue distances within a protein structure, and/or or other molecular modeling calculations is available both publicly (see, for example, the NIH Center for Molecular Modeling, http://cmm.info.nih.gov/modeling) or commercially (from, e.g., Hypercube Inc., Gainesville Fla.; MDL Information Systems, San Leandro, Calif.; Molecular Applications Group, Palo Alto, Calif.; Accelrys, Inc. (formerly Oxford Molecular and, Molecular Simulations Inc., with offices in San Diego, Princeton, N.J. and London, UK; Tripos, Inc., St. Louis, Mo., and the like). One particularly useful program for generation of contact map information is MOE from the Chemical Computing Group (Montreal, Canada). Additional programs for homology modeling include, but are not limited to, SWISS-MODEL (available through Glaxo Wellcome Experimental Research in Geneva, Switzerland) and the WHAT IF program (EMBL). Databases of protein structures that have been obtained by comparative (homology) modeling are available from a number of online sources, and include, but are not limited to, the databases ModBase and 3D Crunch. Likewise, programs for generating and analyzing nucleic acid molecules are utilized for nucleotide sequences; see, for example, "tRNAscan-SE," tRNA analysis software available from Washington University in St. Louis (http://www.genetics.wustl.edu/eddy/tRNAscan-SE). These and other programs known to one of skill in the art can optionally be used to identify two or more elements within a critical distance one another in the tertiary structure of the reference molecule.

Combinations of the above-described techniques can also be used in the preparation of the reference protein contact map. For example, distance measurements not available or not statistically relevant enough from one analysis technique can optionally be generated or confirmed using an alternative technique. One parameter typically employed in the assessment of the protein tertiary structure and generation of the contact map is selection of an acceptable degree of separation, or "critical distance," between the contact amino acids. The critical distance can vary with the nature of the amino acid-amino acid interaction, and can range from about 2.5 to about 7 Angstroms. For example, elements (e.g., sidechains) having ionic bonds or hydrophobic interactions are typically about 4.5 Angstroms apart, while elements in contact via a disulfide bond are about 2.5 Angstroms apart.

In the methods of the present invention, the critical distance between contact amino acid side chains ranges from about 2

Angstroms to about 6.5 (or about 7) Angstroms. Optionally, the critical distance ranges from about 2.5 Angstroms to about 4.5 Angstroms, and typically is less than about 4.5 Angstroms. Thus, for the purposes of the methods of the present invention, any positioning of sidechain elements less than about 5 Angstroms apart is considered a contact pair (e.g., proximal elements). Alternatively, the contact distance can be calculated from the Cα or Cβ of the amino acids, using distances of up to 6.5 Angstroms in these instances.

Sequences and Alignment Protocols

The method of the present invention can be used to identify and/or compare potential crossover positions within two or more parental sequences (e.g., a first sequence, a second sequence, and optional third or additional sequences). Optionally, the sequence of the reference biomolecule can be used as either the first or second sequence. As described previously for the reference molecule, the parental sequences can be provided by any of a number of mechanisms, including, but not limited to, sequencing one or both sequences, providing a nucleic acid sequence for transcription or translation, or querying a nucleic acid or protein database. Additionally, while the sequences of interest can be provided in a physical sense (e.g., isolated or synthesized molecules), preferably they are provided in silico (e.g., as representative sequence strings; see, for example, PCT publication WO 01/75767 (PCT/US01/10231 "METHODS FOR MAKING CHARACTER STRINGS, POLYNUCLEOTIDES AND POLYPEPTIDES HAVING DESIRED CHARACTERISTICS" by Selifonov et al.).

For embodiments of the present invention involving amino acid sequences, the parental sequences typically are derived from a common family of proteins having similar three-dimensional structures (e.g., protein superfamilies). However, the nucleic acid sequences encoding these proteins might or might not share a high degree of sequence identity. In certain embodiments of the present invention, the methods are used to assess crossover positions between "low sequence identity" sequences (e.g., sequences sharing less than 70%, less than 60% or even less than 50% sequence identity).

Sequence similarity/identity of various stringency and length can be detected and recognized using a number of methods or algorithms known to one of skill in the art. For example, many identity or similarity determination methods have been designed for comparative analysis of sequences of biopolymers, for spell-checking in word processing, and for data retrieval from various databases. With an understanding of double-helix pair-wise complement interactions among the four principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package for calculating sequence identity is BLAST, which can be adapted to the present invention by inputting character strings corresponding to the sequences herein.

In certain embodiments of the present invention, one or more of the provided sequences have low sequence identity (sometimes referred to in the art as "low homology sequences" despite the absence of phylogeny considerations) as compared to one another, or to the reference biomolecule. The low identity sequences can be derived from nature, or they can be generated synthetically, mutationally, or computationally. One example of low identity sequences are "codon altered" sequences, as described in, for example, PCT publication WO 00/18906 "Shuffling of Codon Altered Genes" by Patten et al.

After providing the first and second parental sequences, the sequences are aligned with the sequence of the reference protein. In embodiments in which the reference sequence functions as either the first or second sequence, the two sequences are aligned with one another. In other embodiments, a plurality of parental sequences are provided, which are then aligned with either the reference sequence, or with one another. Alignment and comparison of relatively short amino acid sequences (for example, less than about 30 residues) is typically straightforward. Comparison of longer sequences can require more sophisticated methods to achieve optimal alignment of two sequences.

Optimal alignment of sequences can be performed, for example, by a number of available algorithms, including, but not limited to, the "local homology" algorithm of Smith and Waterman (1981 *Adv. Appl. Math.* 2:482), the "homology alignment" algorithm of Needleman and Wunsch (1970 *J. Mol. Biol.* 48:443), the "search for similarity" method of Pearson and Lipman (1988 *Proc. Natl. Acad. Sci. USA* 85:2444), or by computerized implementations of these algorithms (e.g., GAP, BESTFIT, FASTA and TFASTA available in the Wisconsin Genetics Software Package Release 7.0, Genetics Computer Group, 575 Science Dr., Madison, Wis.; and BLAST, see, e.g., Altschul et al., (1977) *Nuc. Acids Res.* 25:3389-3402 and Altschul et al., (1990) *J. Mol. Biol.* 215: 403-410). Alternatively, the sequences can be aligned by inspection. Generally the best alignment (i.e., the relative positioning resulting in the highest percentage of sequence identity over the comparison window) generated by the various methods is selected. However, in certain embodiments of the present invention, the best alignment may alternatively be a superpositioning of selected structural features, and not necessarily the highest sequence identity.

The term "sequence identity" means that two amino acid sequences are identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection. Sequences having "low sequence identity" (sometimes referred to as "low homology" sequences) are sequences having less than about 70%, preferably less than about 60% or more preferably less than about 50% sequence identity over some delineated subsequence of interest.

As applied to polypeptides, the term substantial identity or substantial similarity means that two peptide sequences, when optimally aligned, such as by the programs BLAST, GAP or BESTFIT using default gap weights (described in detail below) or by visual inspection, share at least about 60 to about 80 percent or greater sequence identity or sequence similarity, preferably at least about 90 percent amino acid residue sequence identity or sequence similarity, more preferably at least about 95 percent sequence identity or sequence similarity, or more (including, e.g., about 96, 97, 98, 98.5, 99, or more percent amino acid residue sequence identity or sequence similarity). Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share at least about 60 to about 80 percent or greater sequence identity or sequence similarity, preferably at least about 90 percent amino acid residue sequence identity or sequence similarity, more preferably at least about 95 percent sequence identity or sequence similarity, or more (including, e.g., about 96, 97, 98, 98.5, 99, or more percent nucleotide sequence identity or sequence similarity).

One example of an algorithm that is suitable for determining percent sequence identity or sequence similarity is the FASTA algorithm, which is described in Pearson, W. R. & Lipman, D. J., (1988) *Proc. Natl. Acad. Sci. USA* 85:2444. See also, W. R. Pearson, (1996) *Methods Enzymology* 266: 227-258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Preferred examples of algorithms that are suitable for determining percent sequence identity or sequence similarity are the BLAST and BLAST 2.0 algorithms, which are described in Altschul et al., (1977) *Nuc. Acids Res.* 25:3389-3402 and Altschul et al., (1990) *J. Mol. Biol.* 215:403-410, respectively. BLAST and BLAST 2.0 are used, with the parameters described herein, to determine percent sequence identity or percent sequence similarity for the nucleic acids and polypeptides and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see, Henikoff & Henikoff (1989) *Proc. Natl. Acad. Sci. USA* 89:10915) uses alignments (B) of 50, expectation (E) of 10, M=5, N=−4, and a comparison of both strands.

The BLAST algorithm also performs a statistical analysis of the similarity or identity between two sequences (see, e.g., Karlin & Altschul, (1993) *Proc. Natl. Acad. Sci. USA* 90:5873-5787). One measure of similarity or identity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) *J. Mol. Evol.* 35:351-360. The method used is similar to the method described by Higgins & Sharp, (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) *Nuc. Acids Res.* 12:387-395).

Another preferred example of an algorithm that is suitable for multiple DNA and amino acid sequence alignments is the CLUSTALW program (Thompson, J. D. et al., (1994) *Nuc. Acids Res.* 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) *Proc. Natl. Acad. Sci. USA* 89:10915-10919).

It will be understood by one of ordinary skill in the art, that the above discussion of search and alignment algorithms also applies to identification and evaluation of polynucleotide sequences, with the substitution of query sequences comprising nucleotide sequences, and where appropriate, selection of nucleic acid databases.

Crossover Sites

After providing the parental sequences (e.g., the first sequence, second sequences, and optional additional sequences), portions of the parental sequences are replaced, swapped or exchanged. Each exchange occurs between first and second crossover points on the two parental sequences encompassing the selected region of elements (subsequence of amino acids or nucleotides) of a given exchange. Optionally, multiple subsequences can be swapped at a plurality of crossover positions in a given parental sequence, thereby generating a chimeric biomolecule having more than one subsequence inserted (from one or more parental sequences). With reference to a nucleic acid, the crossover sites define the 5' and 3' ends of the regions of exchanged oligonucleotides (e.g., the positions at which the recombination occurs). For protein sequences, the crossover sites are defined by the start (N-terminus) and end (C-terminus) of the exchanged amino acid residues. In some embodiments, the first crossover site coincides with the 5' end of the nucleic acid, or the N-terminus of the amino acid sequence. In other embodiments, the second crossover site coincides with the 3' end of the nucleic acid, or the C-terminus of the amino acid sequence.

The length of the selected region to be exchanged will vary with the target system. However, the crossover sites employed in the present invention need not provide an identical number of elements for exchange between the two parental sequences. For example, if the crossover sites in the first sequence define a region of 30 elements, the region defined by corresponding crossover sites in the second sequence can optionally contain less than 30 elements or greater than 30 elements.

In the methods of the present invention, one or more "crossover products" (i.e., chimeric sequences) are examined for a given pair or set of parent sequences. In one embodiment, single crossover products are considered; however, the methods of the present invention can be used to generate chimeric recombinants having two or more exchanged regions (e.g., multiple crossover sites). In some embodiments, all of the potential crossover sites for a single exchange are generated for analysis. In other embodiments, only a subset of all possible chimeric products are examined.

Selection of crossover sites can be performed empirically (e.g., starting at every fifth element in the sequence) or the selection can be based upon additional criteria. Considering that co-variation of amino acids during evolution allows proteins to retain a given fold, tertiary structure or function while altering other traits (such as specificity), this information can be useful in selecting possible crossover locations which will not be detrimental to the overall structure or function of the molecule. Alternatively, the regions for exchange can be selected, for example, by targeting a desired activity (e.g., the active site of a protein or catalytic nucleic acid) or specific structural feature (e.g., replacement of alpha helices or strands of a beta sheet). Visual analysis of the alignment of the parent sequence with the contact map and/or tertiary structure of the reference protein can also focus the analytical efforts on regions of structural interest.

Analysis of additional reference parameters assists in the selection of crossover positions and design of recombinant biomolecules. Additional methods for selecting crossover positions for assessment can be found in, for example, PCT publications WO 00/42559 (PCT/US00/01138 "METHODS OF POPULATING DATA STRUCTURES FOR USE IN EVOLUTIONARY SIMULATIONS" by Selifonov and Stemmer), WO 00/42560 (PCT/US00/01202 "METHODS FOR MAKING CHARACTER STRINGS, POLYNUCLEOTIDES AND POLYPEPTIDES HAVING DESIRED CHARACTERISTICS" by Selifonov et al.), WO 01/75767 (PCT/US01/10231 "METHODS FOR MAKING CHARACTER STRINGS, POLYNUCLEOTIDES AND POLYPEPTIDES HAVING DESIRED CHARACTERISTICS" by Selifonov et al.) and U.S. Ser. No. 09/618,579, filed Jul. 18, 2000 ("METHODS FOR MAKING CHARACTER STRINGS, POLYNUCLEOTIDES AND POLYPEPTIDES HAVING DESIRED CHARACTERISTICS" by Gustafsson et al.).

The step of "swapping" the one or more subsequences between parental sequences to generate a chimeric product sequence is performed in silico in the methods of the present invention. In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on crossover site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding in silico recombination methods are found in these applications. This methodology is generally applicable to the present invention in providing for recombination of the in silico and/or the generation of corresponding nucleic acids or proteins.

Scoring the Chimeric Sequences

The methods of the present invention provide mechanisms for evaluating potential crossover positions within the parental sequences, based upon one or more parameters of the chimeric sequence as compared to the reference biomolecule. The methods of the present invention may employ contact maps and contact energy calculations for assessing fitness crossover locations. In the methods of the present invention, the elements of the chimeric molecule are aligned with the contact map, and comparisons are made between the reference sequence and the chimeric sequence. In one embodiment of the methods, the chimeric sequence is compared to the contact map and sets of elements in contact are selected. The selected set(s) of elements in the chimeric molecules are then scored with respect to the corresponding elements in the reference molecule. The scores provide a measure of the likelihood that the chimeric molecule attains a conformation similar to the reference biomolecule, and by inference, acquires a similar conformational stability or desired activity.

One aspect of the comparison and scoring process is the calculation of the contact energies between two or more proximal elements in the chimeric molecule. The contact energy of a selected pair or set of elements can be calculated by a number of procedures known to one of skill in the art. For amino acid sequences, the contact energies can be estimated, for example, using a Miyazawa-Jernigan energy matrix (see, for example, Miyazawa and Jernigan (1999) "Self-consistent estimation of inter-residue protein contact energies based on an equilibrium mixture approximation of residues" *Proteins* 34: 49-68); Miyazawa and Jernigan (1999) "An empirical energy potential with a reference state for protein fold and sequence recognition" Proteins 36: 357-69; Zhang (1998) "Extracting contact energies from protein structures: a study using a simplified model" Proteins 31: 299-308; and Miyazawa, S. & Jernigan, R. L. (1996) "Residue-residue potentials with a favorable contact pair term and an unfavorable high packing density term, for simulation and threading." *J. Mol. Biol.* 256: 623-464.

In this calculation, a 2-dimensional matrix provides interaction strengths between each pairing of amino acids, based upon how often those residues were seen to be in contact in the database of known structures. The reference molecule is examined for proximal amino acid residues deemed to be in contact; two or more residues are considered to be in contact if the interacting atoms of their respective sidechains are less than a critical distance apart. This critical distance can vary with the type of interaction (e.g., hydrophobic, ionic, etc.) but typically is less than about 4.5 to about 5.0 Angstroms. The contact energy is then determined for the chimeric sequence by determining the number of contact pairs (by comparison to the contact map of the reference molecule generated, for example, through one of the above mentioned alignment techniques) and summing the number of contacts (and associated energy values) present in the protein structure. The contact energies generated using a Miyazawa-Jernigan energy matrix are typically dominated by the hydrophobic effect; as such, interactions between positively-charged and negatively-charge amino acid side chains, will be underestimated, as will disulfide-bond (cys-cys) interactions.

Alternatively, the protein contact energies can be calculated using the secondary structure of the contacting residues (such as described by Zhang, C and Kim, S-H. (2000) "Environment-dependent residue contact energies for proteins." *Proc. Natl. Acad. Sci. USA* 97: 2550-2555). For example, using the Zhang-Kim database-dependent matrix, an interaction between a Phe from an α-helix and an Ala from a β-sheet would have a different interaction energy than a Phe from a loop and an Ala from an α-helix. Additional alternative methods for calculating protein contact energies can also be employed in the present methods.

For nucleic acid molecules, any number of position dependent (or position independent) algorithms can be used for comparison purposes. For example, a pair-wise "Smith-Waterman" or "Needleman-Wunsch" alignment function can be used to generate contact energy information (Smith, T. F. and Waterman, M. S. (1981) "Identification of common molecular subsequences" *J. Mol. Biol.* 147: 195-197; Needleman, S. B. & Wunsch, C. D. (1970) "A general method applicable to the search for similarities in the amino acid sequence of two proteins" *J. Mol. Biol.* 48: 443-453). The two algorithms differ in that the sequence comparisons are performed globally using the Needleman-Wunsch algorithm, as opposed to locally using the Smith-Waterman algorithm, thereby forcing an alignment of the entire query sequence versus the reference or database sequence.

In one embodiment of the methods of the present invention, scoring is performed by examining each element of the chimeric sequence and determining if that element is in contact with another element in the sequence. If the selected element is proximal to another element, the contact energy for that pair of proximal elements is calculated. In some embodiments, the scoring includes summing the contact energies for all of the proximal pairs of elements. The "contact energy" component of the scoring step can optionally be weighted by an additional parameter, such as the estimated or measured distance between elements, or the position of the element within the sequence.

In addition to the contact energy parameter, other structural parameters can optionally be included in the scoring process. For example, parameters defining steric bulk, allosteric effects, hydrophobicity or polarizability of the amino acid residue, or overall structural parameters such as structural symmetry, periodicity or patterns in the distribution of component elements, distribution of charge and/or electrostatic fields, orientations of quaternary structural units can also be used for generation of the score. For example, regarding analysis of amino-acid composition and relevant properties, relevant considerations include: hydrophobicity as determined by $\Delta G$ of transfer from solvents, hydrophilicity from column retention, charges on the amino acids, polarity, the $pK_a$ of the amino-acids, bulkiness, side chain entropy, alpha helix/beta sheet propensities, hydration potentials, codon degeneracies and the like.

Furthermore, additional statistical methods can be employed in the scoring of the chimeric sequence. These include, but are not limited to, neural network calculations, Monte Carlo molecular dynamics simulations, multivariate data analyses such as Principal Component Analysis (PCA) and Partial Least Square Projections to Latent Structures (PLS), and other molecular modeling or bioinformatics calculations.

For example, statistical matrixes such as Markov chains can be used to pinpoint ideal crossover locations. Sites within a protein sequence at which amino acid substitutions will more probably cause misfolding of the native conformation can be mapped using a simple on-lattice model, such as that described by Skorobogatiy and Tiana in *Physical Review E* (September 1998) vol. 58, pp. 3572-3577. Neural networks can be used to learn a type of pattern and predict the generated outcome of given variations. (Examples of such neural networks include Schneider and Wrede (1998) "Artificial neural networks for computer-based molecular design" *Prog. Biophys. Mol. Biol.* 70(3):175-222; Schneider et al. (1998) "Peptide design by artificial neural networks and computer-based evolutionary search" *Proc. Natl. Acad. Sci. USA* 95(21): 12179-12184; and Wrede et al. (1998) "Peptide design aided by neural networks: biological activity of artificial signal peptidase I cleavage sites" *Biochemistry* 37(11):3588-35893. Additional examples can be found in WO 00/42559 (Selifonov and Stemmer), WO 00/42560 (Selifonov et al.), WO 01/75767 (Selifonov et al.) and U.S. Ser. No. 09/618,579 (Gustafsson et al.), all supra).

For nucleic acids, one optional approach is the application of multivariate data analysis as described by Jonsson et al. (1993 *Nucl. Acids Res.* 21:733-739) for prediction of strength among a set of defined transcriptional promoters. Thus, in addition to the contact energy information, statistical considerations can be applied to the methods for assessing crossover sites and predicting stability of nucleic acid or protein sequences.

Normalization

In some embodiments of the present invention, the scores generated for the putative contact amino acids in the chimeric molecule are normalized prior to evaluation. In most uses, the chimeric sequences will have a range of sequence identity to the reference sequence. Those chimeras that are closer to the reference sequence will have a better contact score than those that are further in sequence identity to the reference sequence. This can be accounted for either by limiting the chimeras that are used to determine the crossover sites to those that are greater than, for example, about 50% identical, about 60% identical, about 70% identical or greater as compared to the reference protein, or through normalizing the contact energies. This normalization can be done through a linear regression of the chimera's sequence identity to the reference sequence vs. the calculated contact score. The residuals from this regression are then used to determine the optimal crossover positions. Another approach could use a multiple regression of the two or more of the following: length between the two crossover positions, the position of the first crossover, position of the second crossover, and sequence identity between the chimeric product sequence and the reference sequence vs. the calculated contact score. Again, the residuals from the regression could be used to determine the optimal crossover positions.

Generation of Chimeric Products

The methods of the present invention can be employed as prescreening techniques, for assessing the feasibility of potential crossover sites prior to chimeric product synthesis. Optionally, those chimeric products which are assessed favorably (or "pass" this computational pre-screen) are then synthesized and tested in the laboratory. Thus, the methods of the present invention optionally further comprise the step of synthesizing one or more chimeric biomolecule sequences. The chimeric products can be synthesized using any of a variety of techniques known to one of skill in the art. For example, in one embodiment, the chimeric biomolecule is synthesized de novo (using, for example, synthetic chemistry techniques). In another embodiment, the methods include the optional step of expressing the chimeric biomolecule in either a cell-based or a cell-free expression system. Optionally, the step of synthesizing the chimeric biomolecule includes providing the appropriate parental nucleic acids and performing one or more recombination processes. Methodologies for performing the synthesizing step are detailed in the references incorporated herein.

The methods of the present invention optionally include providing constructs comprising one or more of the progeny chimeric nucleic acid sequences. The constructs comprise a vector, such as, a plasmid, a cosmid, a phage, a virus, a bacterial artificial chromosome (BAC), a yeast artificial chromosome (YAC), and the like, into which a chimeric sequence of the present invention has been either generated or inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use of vectors, promoters and many other relevant topics, include Berger et al., supra,; Sambrook et al. (1989), supra, and Ausubel et al. (1989; supplemented through 1999), supra. Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the nucleic acids of the present invention are found in Berger, Sambrook, and Ausubel, as well as Mullis et al., (1987) U.S. Pat. No. 4,683, 202; *PCR Protocols A Guide to Methods and Applications* (Innis et al. eds.) Academic Press Inc. San Diego, Calif. (1990) ("Innis"); Arnheim & Levinson (Oct. 1, 1990) *C&EN* 36-47; *The Journal Of NIH Research* (1991) 3:81-94; Kwoh et al. (1989) *Proc. Natl. Acad. Sci. USA* 86:1173-1177; Guatelli et al. (1990) *Proc. Natl. Acad. Sci. USA* 87:1874-1878; Lomeli et al. (1989) *J. Clin. Chem.* 35:1826-1831; Landegren et al., (1988) *Science* 241:1077-1080; Van Brunt (1990) *Biotechnology* 8:291-294; Wu and Wallace, (1989) *Gene* 4:560-569; Barringer et al. (1990) *Gene* 89:117-122, and Sooknanan and Malek (1995) *Biotechnology* 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369:684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Diversity generating techniques, such as those described below, can be used for generation of additional sequences for use in the methods of the present invention. Furthermore, these diversity generation techniques can be used to modify one or more of the chimeric products. The methods of the present invention optionally further comprise one or more of the following steps: selecting stable or active chimeric products from a library of chimeric molecules generated using various crossover positions, generating diversity in one or more of the product chimeric biomolecules (thereby providing diversified chimeric biomolecules), and recursively repeating the methods of the present invention using sequences from the parental molecules, from one or more chimeric biomolecules, from one or more of the diversified chimeric products as parental sequences, or from a combination thereof.

One group of diversity generating methods is referred to as recombination or DNA shuffling. In these methods, polynucleotides are recombined, either in vitro or in vivo, to generate a library of polynucleotide variants. In recombination-based methods, DNA fragments, PCR amplicons, and/or synthetic oligonucleotides that collectively correspond in sequence to some or all of the sequence of one or more parental polynucleotides are recombined to generate a library of polynucleotide variants of the parental polynucleotide(s). The recombination process may be mediated by hybridization of the DNA fragments, PCR amplicons, and/or synthetic oligonucleotides to each other (e.g., as partially overlapping duplexes), or to a larger piece of DNA, such as a full length template. Depending on the recombination format employed, ligase and/or polymerase may be used to facilitate the construction of a full length polynucleotide. PCR cycling is typically used in formats employing only a polymerase. These methods are generally known to those having ordinary skill in the art and are described extensively elsewhere. See e.g., Soong, N. et al. (2000) *Nat. Genet.* 25(4):436-439; Stemmer, et al. (1999) *Tumor Targeting* 4:1-4; Ness et al. (1999) *Nature Biotechnology* 17:893-896; Chang et al. (1999) *Nature Biotechnology* 17:793-797; Minshull and Stemmer (1999) *Current Opinion in Chemical Biology* 3:284-290; Christians et al. (1999) *Nature Biotechnology* 17:259-264; Crameri et al. (1998) *Nature* 391:288-291; Crameri et al. (1997) *Nature Biotechnology* 15:436-438; Zhang et al. (1997) *Proc. Natl. Acad. Sci. USA* 94:4504-4509; Patten et al. (1997) *Current Opinion in Biotechnology* 8:724-733; Crameri et al. (1996) *Nature Medicine* 2:100-103; Crameri et al. (1996) *Nature Biotechnology* 14:315-319; Gates et al. (1996) *Journal of Molecular Biology* 255:373-386; Stemmer (1996) In: *The Encyclopedia of Molecular Biology*. VCH Publishers, New York. pp. 447-457; Crameri and Stemmer (1995) *BioTechniques* 18:194-195; Stemmer et al., (1995) *Gene,* 164:49-53; Stemmer (1995) "The Evolution of Molecular Computation"

Science 270: 1510; Stemmer (1995) *Bio/Technology* 13:549-553; Stemmer (1994) *Nature* 370:389-391; and Stemmer (1994) *Proc. Natl. Acad. Sci. USA* 91:10747-10751; Giver and Arnold (1998) Current Opinion in Chemical Biology 2:335-338; Zhao et al. (1998) *Nature Biotechnology* 16:258-261; Coco et al. (2001) *Nature Biotechnology* 19:354-359; U.S. Pat. Nos. 5,605,793, 5,811,238, 5,830,721, 5,834,252, 5,837,458, WO 95/22625, WO 96/33207, WO 97/20078, WO 97/35966, WO 99/41402, WO 99/41383, WO 99/41369, WO 99/41368, WO 99/23107, WO 99/21979, WO 98/31837, WO 98/27230, WO 98/27230, WO 00/00632, WO 00/09679, WO 98/42832, WO 99/29902, WO 98/41653, WO 98/41622, and WO 98/42727, WO 00/18906, WO 00/04190, WO 00/42561, WO 00/42559, WO 00/42560, WO 01/23401, WO 00/20573, WO 01/29211, WO 00/46344, and WO 01/29212.

Parental polynucleotides employed in the recombination processes referenced above may be either wildtype polynucleotides or non-naturally occurring polynucleotides. At least one polynucleotide preferably encodes a crossover point selected as described above. In one embodiment of the present invention, chimeric proteins having selected crossover points are prepared by recombination of two or more parental polynucleotides followed by expression. In some embodiments, the parental polynucleotides (at least those not encoding the crossover point) are members of a single gene family. As used herein, the term "gene family" refers to a set of genes that encode polypeptides which exhibit the same type, although not necessarily the same degree, of an activity.

Polynucleic acids can be recombined in vitro by any of a variety of techniques, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described, e.g., in Stemmer (1994) *Proc. Natl. Acad. Sci. USA* 91:10747-10751.

Synthetic recombination methods can also be used, in which oligonucleotides corresponding to targets of interest are chemically synthesized and reassembled in PCR or ligation reactions which include oligonucleotides that correspond to more than one parental polynucleotide, thereby generating new recombined polynucleotides. Oligonucleotides can be made by standard nucleotide addition methods, or can be made, e.g., by tri-nucleotide synthetic approaches. Details regarding such approaches are found in the references noted above, e.g., WO 00/42561 by Crameri et al., "Olgonucleotide Mediated Nucleic Acid Recombination;" WO 01/23401 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

Polynucleotides can also be recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references cited herein.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. These methods can be used in physical systems or can be performed in computer systems according to specific embodiments of the invention. In one method employing a single-stranded template (preferably encoding a crossover point), the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, WO 01/64864.

Methods of recombination can also be performed digitally on an information processing system. For example, algorithms can be used in a computer to recombine sequence strings that correspond to homologous (or even non-homologous) bio-molecules. According to specific embodiments of the invention, after processing in a computer system, the resulting sequence strings can be converted into nucleic acids by synthesis of nucleic acids which correspond to the recombined sequences, e.g., in concert with oligonucleotide synthesis/gene reassembly techniques. This approach can generate random, partially random, or designed variants. Many details regarding various embodiments of computer enabled recombination, including the use of various algorithms, operators and the like in computer systems, as well as combinations of designed nucleic acids and/or proteins (e.g., based on crossover site selection) as well as designed, pseudo-random or random recombination methods are described in WO 00/42560 by Selifonov et al., "Methods for Making Character Strings, Polynucleotides and Polypeptides Having Desired Characteristics," WO 01/75767 by Gustafsson et al., "In Silico Cross-Over Site Selection," and WO 00/42559 by Selifonov and Stemmer "Methods of Populating Data Structures for Use in Evolutionary Simulations."

Directed Evolution

Directed evolution (or alternatively "artificial evolution") can be carried out by practicing one or more diversity generating methods in a reiterative fashion coupled with screening (described in more detail elsewhere herein) to generate a further set of recombinant nucleic acids. Thus, directed or artificial evolution can be carried out by repeated cycles of mutagenesis and/or recombination and screening. For example, mutagenesis and/or recombination can be carried out on parental polynucleotides (selected to provide a desired crossover point) to generate a library of variant polynucleotides that are then expressed to generate proteins having the crossover point that are screened for a desired activity. One or more variant proteins may be identified from these proteins as exhibiting improvement in the desired activity. The identified proteins can be reverse translated to ascertain one or more polynucleotide sequences that encode the identified protein variants, which in turn can be mutated or recombined in a subsequent round of diversity generation and screening.

Directed evolution using recombination-based formats of diversity generation is described extensively in the references cited herein. Directed evolution using mutagenesis as the basis for diversity generation is also well known in the art. For example, recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are described in Arkin & Youvan (1992) *Proc. Natl. Acad. Sci. USA* 89:7811-7815. Similarly, exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11: 1548-1552.

Crossover identification methods of the present invention are useful in optimizing the directed evolution process regardless of the diversity generating procedure employed. Crossover information derived from application of the invention can be used to more intelligently design libraries made in a directed evolution process. For example, where it is desired to insert a crossover point at certain amino acid residue positions, synthetic oligonucleotides incorporating the codons encoding those desired amino acid residues from two or more parents can be used in one of the recombination formats referred to herein to generate a polynucleotide variant library that can then be expressed. Alternatively, the desired crossover points can be incorporated using one of the various mutagenesis methods described herein. In any event, the resulting protein variant library will thus contain protein variants that incorporate what are believed to be beneficial residues or potentially beneficial residues. This process can be repeated until a protein variant having the desired activity is identified.

Screening/Selection for Activity

Polynucleotides generated in connection with methods of the present invention are optionally cloned into cells for activity screening (or used in in vitro transcription reactions to make products which are screened). Furthermore, the nucleic acids can be enriched, sequenced, expressed, amplified in vitro or treated in any other common recombinant method.

General texts that describe molecular biological techniques useful herein, including cloning, mutagenesis, library construction, screening assays, cell culture and the like include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 (Sambrook) and *Current Protocols in Molecular Biology*, F. M. Ausubel et al., eds., Current Protocols, a joint venture between Greene Publishing Associates, Inc. and John Wiley & Sons, Inc., New York (supplemented through 2000) (Ausubel)). Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley-Liss, New York (1994)) and the references cited therein, Humason (*Animal Tissue Techniques*, fourth edition W.H. Freeman and Company (1979)) and Ricciardelli, et al., *In Vitro Cell Dev. Biol.* 25:1016-1024 (1989). References for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS).

In one preferred method, reassembled sequences are checked for incorporation of family-based recombination oligonucleotides. This can be done by cloning and sequencing the nucleic acids, and/or by restriction digestion, e.g., as essentially taught in Sambrook, Berger and Ausubel, supra. In addition, sequences can be PCR amplified and sequenced directly. Thus, in addition to, e.g., Sambrook, Berger, Ausubel and Innis (supra), additional PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8): 1611-1617). In the methods, four PCR reactions on a template are performed, in each of which one of the nucleotide triphosphates in the PCR reaction mixture is partially substituted with a 2'deoxynucleoside 5'-[P-borano]-triphosphate. The boronated nucleotide is stochastically incorporated into PCR products at varying positions along the PCR amplicon in a nested set of PCR fragments of the template. An exonuclease that is blocked by incorporated boronated nucleotides is used to cleave the PCR amplicons. The cleaved amplicons are then separated by size using polyacrylamide gel electrophoresis, providing the sequence of the amplicon. An advantage of this method is that it uses fewer biochemical manipulations than performing standard Sanger-style sequencing of PCR amplicons.

Synthetic genes are amenable to conventional cloning and expression approaches; thus, properties of the genes and proteins they encode can readily be examined after their expression in a host cell. Synthetic genes can also be used to generate polypeptide products by in vitro (cell-free) transcription and translation. Polynucleotides and polypeptides can thus be examined for their ability to bind a variety of predetermined ligands, small molecules and ions, or polymeric and heteropolymeric substances, including other proteins and polypeptide epitopes, as well as microbial cell walls, viral particles, surfaces and membranes.

For example, many physical methods can be used for detecting polynucleotides encoding phenotypes associated with catalysis of chemical reactions by either polynucleotides directly, or by encoded polypeptides. Solely for the purpose of illustration, and depending on the specifics of particular pre-determined chemical reactions of interest, these methods may include a multitude of techniques well known in the art which account for a physical difference between substrate(s) and product(s), or for changes in the reaction media associated with chemical reaction (e.g. changes in electromagnetic emissions, adsorption, dissipation, and fluorescence, whether UV, visible or infrared (heat)). These methods also can be selected from any combination of the following: mass-spectrometry; nuclear magnetic resonance; isotopically labeled materials, partitioning and spectral methods accounting for isotope distribution or labeled product formation; spectral and chemical methods to detect accompanying changes in ion or elemental compositions of reaction product(s) (including changes in pH, inorganic and organic ions and the like). Other methods of physical assays, suitable for use in the methods herein, can be based on the use of biosensors specific for reaction product(s), including those comprising antibodies with reporter properties, or those based on in vivo affinity recognition coupled with expression and activity of a reporter gene. Enzyme-coupled assays for reaction product detection and cell life-death-growth selections in vivo can also be used where appropriate. Regardless of the specific nature of the physical assays, they all are used to select a desired activity, or combination of desired activities, provided or encoded by a biomolecule of interest.

The specific assay used for the selection will depend on the application. Many assays for proteins, receptors, ligands and the like are known. Formats include binding to immobilized components, cell or organismal viability, production of reporter compositions, and the like.

High throughput assays are particularly suitable for screening crossover-based libraries employed in the present invention. In high throughput assays, it is possible to screen up to several thousand different variants in a single day. For example, each well of a microtiter plate can be used to run a separate assay, or, if concentration or incubation time effects are to be observed, every 5-10 wells can test a single variant (e.g., at different concentrations). Thus, a single standard microtiter plate can assay about 100 (e.g., 96) reactions. If 1536 well plates are used, then a single plate can easily assay from about 100 to about 1500 different reactions. It is possible to assay several different plates per day; assay screens for up to about 6,000-20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.) which can provide very high throughput microfluidic assay methods.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols for various high throughput screening assays. Thus, for example, Zymark Corp. provides technical bulletins describing screening systems for detecting the modulation of gene transcription, ligand binding, and the like.

A variety of commercially available peripheral equipment and software is available for digitizing, storing and analyzing a digitized video or digitized optical or other assay images, e.g., using PC (Intel x86 or pentium chip-compatible DOS™, OS2™, WINDOWS™, or WINDOWS NT™ based machines), MACINTOSH™, or UNIX based (e.g., SUN™ work station) computers.

Systems for analysis typically include a digital computer with software for directing one or more step of one or more of the methods herein, and, optionally, also include, e.g., high-throughput liquid control software, image analysis software, data interpretation software, a robotic liquid control armature for transferring solutions from a source to a destination operably linked to the digital computer, an input device (e.g., a computer keyboard) for entering data to the digital computer to control operations or high throughput liquid transfer by the robotic liquid control armature and, optionally, an image scanner for digitizing label signals from labeled assay components. The image scanner can interface with image analysis software to provide a measurement of probe label intensity. Typically, the probe label intensity measurement is interpreted by the data interpretation software to show whether the labeled probe hybridizes to the DNA on the solid support.

In some embodiments, cells, viral plaques, spores or the like, comprising in vitro oligonucleotide-mediated recombination products or physical embodiments of in silico recombined nucleic acids, can be separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each parameter can be controlled and optimized.

The uniform process of automated colony picking such as the Q-bot decreases human handling error and increases the rate of establishing cultures (roughly 10,000/4 hours). These cultures are optionally shaken in a temperature and humidity controlled incubator. Optional glass balls in the microtiter plates act to promote uniform aeration of cells and the dispersal of cellular (e.g., mycelial) fragments similar to the blades of a fermentor. Clones from cultures of interest can be isolated by limiting dilution. As also described supra, plaques or cells constituting libraries can also be screened directly for the production of proteins, either by detecting hybridization, protein activity, protein binding to antibodies, or the like. To increase the chances of identifying a pool of sufficient size, a prescreen that increases the number of mutants processed by 10-fold can be used. The goal of the primary screen is to quickly identify mutants having equal or better product titers than the parent strain(s) and to move only these mutants forward to liquid cell culture for subsequent analysis.

One approach to screening diverse libraries is to use a massively parallel solid-phase procedure to screen cells expressing polynucleotide variants, e.g., polynucleotides that encode enzyme variants. Massively parallel solid-phase screening apparatus using absorption, fluorescence, or FRET are available. See, e.g., U.S. Pat. No. 5,914,245 to Bylina, et al. (1999); see also, http://www.kairos-scientific.com/; Youvan et al. (1999) "Fluorescence Imaging Micro-Spectrophotometer (FIMS)" *Biotechnology et alia*, <www.et-al.com> 1:1-16; Yang et al. (1998) "High Resolution Imaging Microscope (HIRIM)" *Biotechnology et alia*, <www.et-al.com> 4:1-20; and Youvan et al. (1999) "Calibration of Fluorescence Resonance Energy Transfer in Microscopy Using Genetically Engineered GFP Derivatives on Nickel Chelating Beads" posted at www.kairos-scientific.com. Following screening by these techniques, molecules of interest are typically isolated, and optionally sequenced using methods that are well known in the art. The sequence information is then used as set forth herein to design a new protein variant library.

Similarly, a number of well-known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual synthetic operations performed by a scientist. Any of the above devices are suitable for use with the present invention, e.g., for high-throughput screening of molecules encoded by nucleic acids evolved as described herein. The nature and implementation of modifications to these devices (if any) so that they can operate as discussed herein will be apparent to persons skilled in the relevant art.

Systems

As should be apparent, embodiments of the present invention employ processes acting under control of instructions and/or data stored in or transferred through one or more computer systems. Embodiments of the present invention also relate to apparatus for performing these operations. Such apparatus may be specially designed and/or constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein. In some cases, however, it may be more convenient to construct a specialized apparatus to perform the required method operations. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, magnetic tape; optical media such as CD-ROM devices and holographic devices; magneto-optical media; semiconductor memory devices, and hardware devices that are specially configured to store and perform program instructions, such as read-only memory devices (ROM) and random access memory (RAM), and sometimes application-specific integrated circuits (ASICs), programmable logic devices (PLDs) and signal transmission media for delivering computer-readable instructions, such as local area networks, wide area networks, and the Internet. The data and program instructions of this invention may also be embodied on a carrier wave or other transport medium (e.g., optical lines, electrical lines, and/or airwaves).

The present invention provides a computer or computer-readable medium with instructions for selecting and/or assessing crossover sites in a protein sequence. The computer or computer-readable medium includes one or more computer codes or algorithms that perform one or more of the following functions: i) inputs a sequence of a reference biomolecule or biomolecular structure, ii) generates a contact map for the reference sequence of the reference molecule; iii) aligns a first sequence and a second sequences with the reference sequence; iv) swaps one or more subsequences between the first and second parental sequences to produce a chimeric sequence; v) compares the chimeric sequence with the contact map to select a two or more elements in the chimeric sequence that correspond to proximal elements in contact in the reference molecule (according to the contact map); and vi) scores the selected residues. Optionally, the swapping step is repeated for a plurality of possible subsequences or sets of subsequences, thereby generating a library, or plurality, of chimeric sequences for analysis. The computer-generated score thus provides a measure of the likelihood that a chimeric sequence retains the structure, conformational stability, and/or activity of the reference molecule. Software of this invention may also provide any of the other logical operations described herein.

Identification of best locations for bridging oligonucleotides can be used to generate a diverse yet structurally stable library of chimeric progeny (or "shufflants"). Generally, in prior work, this analysis has only been approached by considering chimeras from one or two crossovers. However, this does not take into account the effect of multiple crossovers in a library. Optionally, a plurality of sequences (e.g., 3 or more) can be used in the methods of the present invention. For example, the present invention also provides a method of identifying a plurality of possible crossover locations that will result in a stable library, based on an in silico analysis of a full (or nearly full) chimeric library. Optionally, the plurality of crossover positions includes about 50%, about 75%, about 85%, about 90%, about 95%, about 98%, about 99% or about 100% (e.g., all or substantially all) possible crossover locations that will result in a stable library.

Optionally, the computer generates a plurality of chimeric sequences from two or more parental sequences, thereby assessing multiple crossover sites in the sequence of interest. In one embodiment of the method, an initial number of crossovers, n, is determined based on the number of parent sequences employed, m, and a maximum number of sequences (MAX) that can be computationally analyzed, using the following equation. Max=$m^n$−1. Based upon current hardware, for example, the value of MAX is about $10^{10}$ sequences; however, this value will increase as computing technologies improve. Initial crossovers are then distributed equally (or asymmetrically) throughout the length of the sequences. Optionally, the parent set of crossovers is chosen (for example, by a user) based on additional information (including, but not limited to, structural considerations, homology, enzyme activity, etc.). The entire library of possible unmutated chimeras (X) is then created in silico.

In one embodiment of the method, the computer of the present invention inputs the sequence of the biomolecule, for example, an amino acid sequence of a reference protein. The reference sequence can be input from any of a number of sources, including experimentally generated data (e.g., sequencing data), data originating from previous recombination products, public and/or commercial databases, and the like. The computer (or computer medium) then generates a contact map for the reference molecule, by any of a number of procedures or algorithms available in the art (and as described previously).

Alternatively, the computer of the present invention inputs the sequences of a first parental biomolecule, a second parental biomolecule, and optionally, additional parental biomolecules (e.g., a plurality of biomolecular sequences), and the sequences are aligned with one another in the absence of a reference sequence.

The computer then swaps, or substitutes, a subsequence (a selected region of the sequence defined by first and second crossover sites in the parent sequence) between two parental sequence to produce a chimeric sequence. Optionally, the computer performs the swapping procedure a plurality of times, using different subsequences from the two parental sequences, or using subsequences from a plurality of parental sequences, thereby generating one or more chimeric sequences having one or more crossover sites.

After generation of the chimeric sequence by swapping regions between the two (or more) parental sequences, the computer compares the elements of the chimeric sequence to the contact map. The computer selects those chimeric elements which correspond to proximal elements in the reference sequence, and scores those elements. In one embodiment, the scoring performed by the computer is based upon one or more parameters, such as calculated contact energies, steric hindrances, hydrophobic nature or polarizability.

In one embodiment, the comparing and scoring steps are based upon energies of the chimeric sequences. There are numerous ways of calculating the energy of the chimeric library. For example, energy terms can be calculated based upon a Miyazawa-Jernigan matrix, as described above. This energy term is typically calculated from the sum of the energies of residue contacts expected to be in the chimeric progeny. A normalized energy is optionally computed for each possible chimera given the set of crossovers.

In certain embodiments of the present invention, chimeric sequences with the lowest calculated energy are then statistically analyzed. For example, correlation coefficients can be calculated by a number of methods, including, but not limited to, Bayesian analysis, neural networks, etc. A high correlation coefficient between two adjacent blocks of sequences indicates that the crossover is poorly positioned, due to the fact that the same sequence for the block before the crossover is favored for the block after the crossover.

Tables 1 and 2 show the exemplary results for an initial set of crossover positions. These crossovers are then repositioned and the energy calculations repeated until the correlation coefficient indicates that the crossover is in a favorable position. If there is no favorable position for a crossover between two neighboring crossovers (e.g., two crossover subsequences defined by an intermediate crossover are highly correlated), then no intermediate crossover between the two neighbors is included in the set. Once all crossovers are in favorable positions, the entire process is repeated with a new set of initial crossovers. The set of crossovers that generates the chimeric library with the lowest calculated energy is then chosen. This set can then be used in further activities, such as in a laboratory experiment. As an example, Table 2 illustrates correlation coefficients between sequence blocks for a set of crossover locations in between three MLE (Maximum Likelihood Estimation) sequences. Cells containing an "XXX" indicate high correlation coefficients between sequential sequence blocks and thus poor crossover locations.

TABLE 1

SEQUENCE BLOCKS

| | 1 | 2 | 3 | 4 | 5 | 6 | 7 | 8 | 9 | 10 | 11 |
|---|---|---|---|---|---|---|---|---|---|---|---|
| 1 | 1.000 | 0.030 | 0.618 | 0.039 | 0.001 | 0.004 | −0.049 | 0.114 | 0.214 | 0.156 | 0.604 |
| 2 | 0.030 | 1.000 | 0.017 | −0.024 | 0.001 | 0.001 | 0.023 | −0.031 | 0.046 | 0.047 | 0.005 |
| 3 | 0.612 | 0.017 | 1.000 | 0.034 | 0.001 | 0.011 | 0.055 | 0.012 | 0.131 | 0.191 | 0.440 |
| 4 | 0.039 | −0.024 | 0.034 | 1.000 | 0.331 | 0.123 | 0.051 | −0.020 | −0.014 | 0.020 | 0.020 |
| 5 | 0.001 | 0.001 | 0.001 | XXX | 1.000 | 0.632 | 0.026 | −0.022 | −0.008 | −0.004 | 0.001 |
| 6 | 0.004 | 0.001 | 0.011 | 0.123 | XXX | 1.000 | 0.008 | −0.001 | 0.005 | 0.010 | 0.009 |
| 7 | −0.049 | 0.023 | 0.055 | 0.051 | 0.026 | 0.008 | 1.000 | −0.403 | 0.019 | 0.045 | 0.000 |
| 8 | 0.114 | −0.031 | 0.012 | −0.020 | −0.022 | −0.001 | −0.403 | 1.000 | −0.062 | −0.060 | 0.038 |
| 9 | 0.214 | 0.046 | 0.131 | 0.014 | −0.008 | 0.005 | 0.019 | −0.062 | 1.000 | 0.148 | 0.141 |
| 10 | 0.155 | 0.047 | 0.191 | 0.020 | −0.004 | 0.010 | 0.045 | −0.060 | 0.148 | 1.000 | 0.242 |
| 11 | 0.604 | 0.006 | 0.494 | 0.020 | 0.002 | 0.009 | 0.000 | 0.038 | 0.141 | 0.242 | 1.000 |

TABLE 2

PAIRWISE CORRELATION COEFFICIENTS BETWEEN SEQUENCE BLOCKS

| Variable | by Variable | Correlation | Count | Signif Prob |
|---|---|---|---|---|
| 2 | 1 | 0.0300 | 1196 | 0.2999 |
| 3 | 1 | 0.6117 | 1196 | 0.0000 |
| 3 | 2 | 0.0167 | 1196 | 0.5630 |
| 4 | 1 | 0.0394 | 1196 | 0.1730 |
| 4 | 2 | −0.0244 | 1196 | 0.3985 |
| 4 | 3 | 0.0344 | 1196 | 0.2347 |
| 5 | 1 | 0.0011 | 1196 | 0.9700 |
| 5 | 2 | 0.0010 | 1196 | 0.9719 |
| 5 | 3 | 0.0011 | 1196 | 0.9699 |
| 5 | 4 | 0.3307 | 1196 | 0.0000 |
| 6 | 1 | 0.0041 | 1196 | 0.8862 |
| 6 | 2 | 0.0007 | 1196 | 0.9816 |
| 6 | 3 | 0.0109 | 1196 | 0.7058 |
| 6 | 4 | 0.1232 | 1196 | 0.0000 |
| 6 | 5 | 0.6319 | 1196 | 0.0000 |
| 7 | 1 | −0.0492 | 1196 | 0.0888 |
| 7 | 2 | 0.0234 | 1196 | 0.4184 |
| 7 | 3 | 0.0546 | 1196 | 0.0592 |
| 7 | 4 | 0.0511 | 1196 | 0.0774 |
| 7 | 5 | 0.0264 | 1196 | 0.3620 |
| 7 | 6 | 0.0085 | 1196 | 0.7698 |
| 8 | 1 | 0.1139 | 1196 | 0.0001 |

TABLE 2-continued

PAIRWISE CORRELATION COEFFICIENTS BETWEEN SEQUENCE BLOCKS

| Variable | by Variable | Correlation | Count | Signif Prob | c | −.8 | .6 | .4 | .2 | .2 | .4 | .6 | .8 |
|---|---|---|---|---|---|---|---|---|---|---|---|---|---|
| 8 | 2 | −0.0312 | 1196 | 0.2814 | | | | | | | | | |
| 8 | 3 | 0.0118 | 1196 | 0.6826 | | | | | | | | | |
| 8 | 4 | −0.0200 | 1196 | 0.4897 | | | | | | | | | |
| 8 | 5 | −0.0223 | 1196 | 0.4406 | | | | | | | | | |
| 8 | 6 | −0.0012 | 1196 | 0.9669 | | | | | | | | | |
| 8 | 7 | −0.4032 | 1196 | 0.0000 | | | | | | | | | |
| 9 | 1 | 0.2141 | 1196 | 0.0000 | | | | | | | | | |
| 9 | 2 | 0.0465 | 1196 | 0.1080 | | | | | | | | | |
| 9 | 3 | 0.1313 | 1196 | 0.0000 | | | | | | | | | |
| 9 | 4 | 0.0144 | 1196 | 0.6196 | | | | | | | | | |
| 9 | 5 | −0.0077 | 1196 | 0.7915 | | | | | | | | | |
| 9 | 6 | 0.0052 | 1196 | 0.8576 | | | | | | | | | |
| 9 | 7 | 0.0191 | 1196 | 0.5095 | | | | | | | | | |
| 9 | 8 | −0.0616 | 1196 | 0.0331 | | | | | | | | | |
| 10 | 1 | 0.1555 | 1196 | 0.0000 | | | | | | | | | |
| 10 | 2 | 0.0466 | 1196 | 0.1070 | | | | | | | | | |
| 10 | 3 | 0.1914 | 1196 | 0.0000 | | | | | | | | | |
| 10 | 4 | 0.0197 | 1196 | 0.4950 | | | | | | | | | |
| 10 | 5 | −0.0042 | 1196 | 0.8857 | | | | | | | | | |
| 10 | 6 | 0.0099 | 1196 | 0.7327 | | | | | | | | | |
| 10 | 7 | 0.0454 | 1196 | 0.1168 | | | | | | | | | |
| 10 | 8 | −0.0598 | 1196 | 0.0386 | | | | | | | | | |
| 10 | 9 | 0.1483 | 1196 | 0.0000 | | | | | | | | | |
| 11 | 1 | 0.6044 | 1196 | 0.0000 | | | | | | | | | |
| 11 | 2 | 0.0058 | 1196 | 0.8406 | | | | | | | | | |
| 11 | 3 | 0.938 | 1196 | 0.0000 | | | | | | | | | |

Optionally, the code of the computer or computer-readable medium includes a mechanism or algorithm for normalizing the scores generated for the contact pairs. For example, the computer or computer-readable medium can perform a multiple regression and provide residual values as coefficients of variation. Optionally, the normalization operation is performed either prior to presenting the raw score to the user, or upon further instruction from the user after presentation of the raw score. In one embodiment of the present invention, the score is presented as a triangular contour plot.

Logical instructions for performing the above-described calculations can be constructed by one of skill using a standard programming language such as C, C++, Visual Basic, Fortran, Basic, Java, or the like. For example, a computer can include software for searching a database for the first and second sequences, and optionally modified for communication with a user interface (e.g., a GUI in a standard operating system such as a Windows, Macintosh, UNIX, LINUX, and the like), to obtain the sequence strings, align the component elements, perform the calculations, and/or manipulate the examination results (e.g., the assessment of crossover positions). Standard desktop applications including, but not limited to, word processing software (e.g., Microsoft Word™ or Corel WordPerfect™), spreadsheet and/or database software (e.g., Microsoft Excel™, Corel Quattro Pro™, Microsoft Access™, Paradox™, Filemaker Pro™, Oracle™, Sybase™, and Informix™) and the like, can be adapted for these (and other) purposes.

The computer-readable media of the present invention include, but are not limited to, optical media, magnetic media, and dynamic memory, flash memory, and static memory. Optionally, the computer or computer readable medium can provide the analysis results in the form of an output file. The output file can, for example, be in the form of a graphical representation of part or all of the aligned first, second and/or reference sequences, or in the form of a matrix (such as the Miyazawa-Jemigan matrix).

Web-Based Libraries of Chimeric Sequences

Various embodiments of the present invention relate to methods and/or systems for determining and or using information derived from chimeric data sequences or biomolecules (e.g., RNA, DNA, proteins, etc.) of interest. The present invention, in specific embodiments, further comprises methods and/or systems for providing libraries of chimeric sequence data, enabling a client to generate or analyze one or more sets of chimeric sequences, structures, and/or contact maps.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. The following examples are offered to illustrate, but not to limit the claimed invention.

One family of proteins of interest is the muconate lactonizing enzymes (MLEs), also known as muconate cycloisomerases. These enzymes are essential for the degradation of aromatic compounds to citric acid cycle intermediates. MLEs encode proteins with conserved structures and some functional diversity. MLE I functions within the β-ketoadipate pathway to catalyze the conversion of cis,cis-muconate into (4S)-muconolactone (Ngai, K., Ormston, L. N. & Kallen, R. G. (1983) "Enzymes of the beta-ketoadipate pathway in *Pseudomonas putida*: kinetic and magnetic resonance studies of cis,cis-muconate cycloisomerase catalyzed reaction." *Biochemistry* 22:5223-5230). MLE II catalyzes the same cycloisomerization reaction but uses 3-chloromuconate as a substrate (Schmidt, E. & Knackmuss, H.-J. (1980) "Chemical structure and biodegradability of halogenated aromatic compounds." *Biochem. J.* 192: 339-347). Structures of the two enzymes solved to 3 Å (MLE II) and 1.85 Å (MLE I) are very similar: both comprise an α/β barrel with an N-terminal capping domain and have an average RMSD of 0.96 Å (Kleywegt, G. J. & Jones, T. A. (1996) "A re-evaluation of the crystal structure of chloromuconate cycloisomerase." *Acta. Crystallogr. Sect.D* 52: 858; and Helin, S., Kahn, P. C., Guha, B. L., Mallows, D. G. & Goldman, A. (1995) "The refined X-ray structure of muconate lactonizing enzyme from pseudomonas putida PRS2000 at 1.85 resolution." *J Mol Biol.* 254: 918-841). As members of the enolase superfamily, they represented an ideal case for "low sequence identity" recombination of sequences having less than about 60% sequence identity (often incorrectly referred to as "low homology" recombination).

In these experiments we have sought to derive structural information computationally and direct recombination accordingly. As parental sequences, we chose three muconate lactonizing enzymes (MLEs) with pairwise amino acid sequence identities between about 40 and 52%: MLE II from *Pseudomonas putida*, and MLE I from *P. putida* and *Acinetobacter calcoaceticus* (accession numbers P27099, AAA66202.1 and Q43931, respectively). Crossovers were designed for ten positions throughout the MLE sequences representing positions predicted to be either disruptive or not disruptive to structural stability. These were tested using experimental recombination; the results indicate that the computational model can be used to design multiple functional chimeras of three MLEs.

We have used structural information to choose recombination points among these genes. Based on these computational results, oligonucleotides were synthesized and used to direct recombination, thereby producing libraries of chimeric biomolecules. From these libraries we selected chimeric products that retained activity for cis,cis-muconate. We found multiple different active enzymes containing blocks of sequence from two or three different MLEs. These variants have comparable in vivo function to that of the most active wild type parent, and contain crossover sites strongly biased towards those that we predict to be favorable, while sites predicted to be unfavorable are strongly selected against. We conclude that computational "prescreening" of chimeric sequences allows us to select optimal recombination positions, thereby increasing fitness of a library and decreasing the number of variants that must be screened.

Design of an Algorithm for Predicting Chimeric Protein Stabilities by Calculating Contact Energies We designed an algorithm to assess in silico the stability of chimeric proteins. The algorithm uses a known reference sequence and structure (in this example, MLE I from *P. putida*) to define which amino acids are in contact with one another (e.g., a contact map). The algorithm also aligns all of the parental sequences with each other and uses the alignment to generate chimeric full-length sequences in silico. In the simplest case, this corresponds to replacing a single section of one parental protein with the corresponding segment from a second parent. To assess the effect of amino acid substitutions relative to the reference sequence, the change in contact energy, $\Delta E_C$, is calculated by comparing the chimeric sequences with the reference sequence, using a contact energy function derived as described by Miyazawa, et. al. (see Miyazawa, S. & Jernigan, R. L. (1996 "Residue-residue potentials with a favorable contact pair term and an unfavorable high packing density term, for simulation and threading." *J. Mol. Biol.* 256: 623-464, and additional references supra).

Figure 2A:
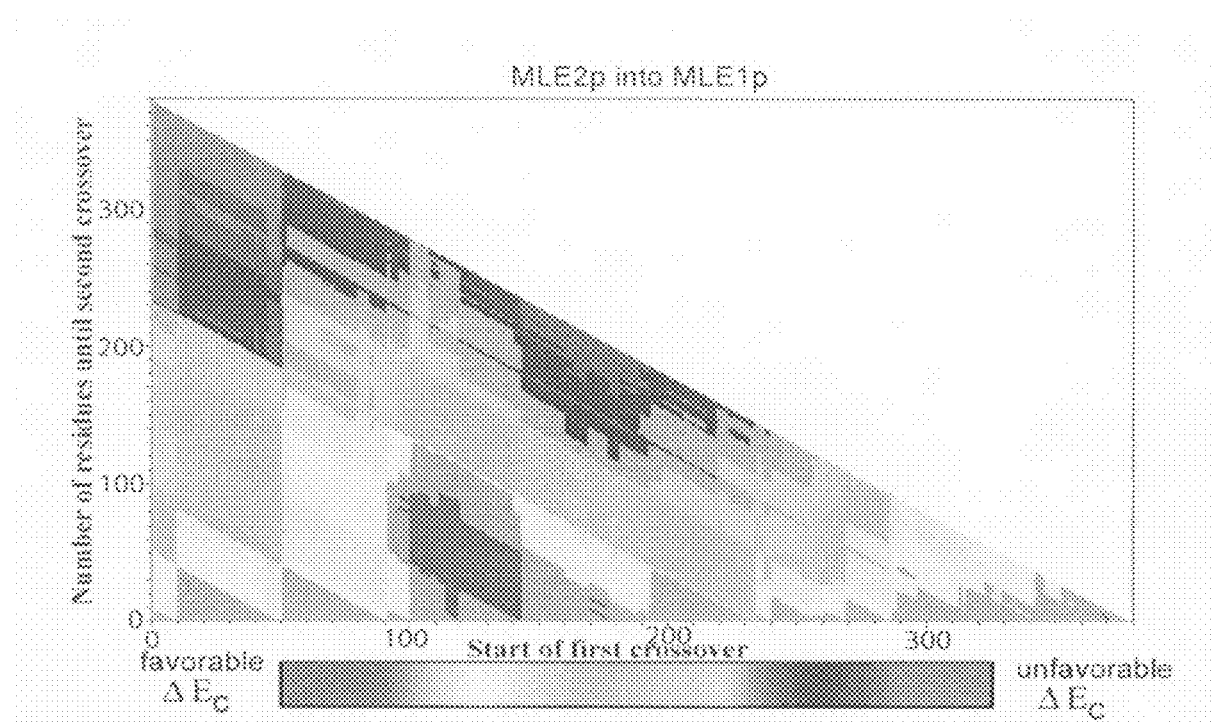

FIG. 2A shows a map of the predicted contact energy changes for chimeric MLE proteins in which a single segment of donor protein *P. putida* MLE II replaces the corresponding segment of reference protein *P. putida* MLE I. The ordinate (x-axis) shows the location along the linear sequence at which the replacement begins (e.g., the first crossover position), and the abscissa (y-axis) shows the length of the replacement. Replacements where the chimera contains amino acids whose contact is less favorable than the reference sequence are shown in magenta and reflect changes likely to lead to structural disruption. Positions where the predicted chimera contains amino acids whose contact is more favorable than the reference sequence are shown in red and represent changes that are likely to be structurally acceptable. Positions of the high degrees of disruption, high contact score, are shown in purple. As the length increases, the contact score also increases. This is due to increased differences between the chimeras and the original contact map.

Figure 2B:
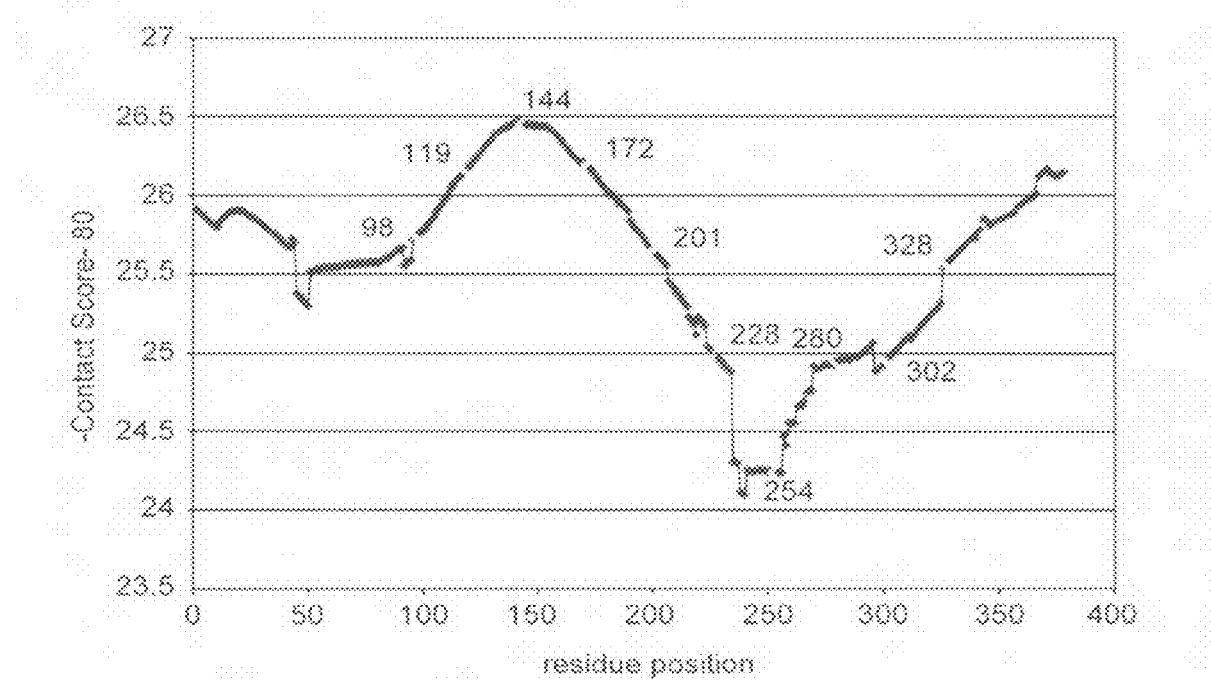

Predictions of Chimeric Protein Stability can be Used to Specify Crossover Points Our aim in developing the algorithm was to design libraries of chimeras in which crossover positions are selected based on the likelihood that they would work well as one of multiple crossovers, rather than as a single crossover. To achieve this, we calculated the average $\Delta E_C$ when segments of donor protein of different lengths (from 1-80 amino acids) are inserted beginning or ending at a specific position in the reference protein. FIG. 2B shows the average contact energy changes when 1-80 amino acids from *P. putida* MLE II replace the corresponding segment of reference protein *P. putida* MLE I. The results are very similar when *A. calcoaceticus* MLE I is used as the donor instead of *P. putida* MLE II (data not shown).

Ten crossover positions were chosen based on the curves indicated by the residue position labels in FIG. 2B. A lower position on the abscissa of FIG. 2B denotes a larger $\Delta E_C$ and consequently a crossover point that is likely to be more structurally disruptive; we chose positions that represented a full range of $\Delta E_C$ values and were evenly distributed throughout the structure. The crossover positions predicted by the in silico algorithm to be optimal display low contact scores for chimeras where the first crossover is at that position as well as for chimeras where the second crossover is at the position. Here we have chosen ten crossover sites that represent positions predicted to have both high and low contact energies in order to test the predictive power of this model. The crossovers sites are distributed evenly throughout the α/β barrel in the center of the loops connecting the helices and sheets. These crossover sites are at residue positions 98, 119, 144, 172, 201, 228, 254, 280, 302, and 328 in the MLE alignment. Crossover positions 119, 144, 172, 201, and 328 are predicted to be favorable whereas 98, 228, 254, 280 and 302 are predicted to be unfavorable. These calculations were based on the monomer structure, however, the calculations repeated with the octomeric structure provided the same predictions. We then tested our computational predictions by forcing recombination at all 10 positions, selecting functional variants and determining whether crossover sites predicted to be favorable are those found in the functional chimeric proteins.

Oligonucleotide-Mediated Recombination

We chose MLE parental sequences lacking sufficient sequence identity to recombine with one another in a standard shuffling reaction (see, for example, Moore, G. L., Maranas, C. D., Lutz, S. & Benkovic, S. J. (2001) "Predicting crossover generation in DNA shuffling." *Proc. Natl. Acad. Sci. USA* 98: 3226-3231). This enabled us to test our specific predictions thoroughly; by allowing recombination at only a small number of positions, we could obtain statistically-meaningful data by analyzing a relatively small number of variants.

To facilitate "low sequence identity" recombination, crossover oligonucleotides were synthesized to generate recombinations at ten positions throughout the MLE sequences. The oligos were designed such that half of the oligo is identical to one sequence and the other half is identical to another sequence, thereby encouraging recombination between the two sequences. The degree of recombination was sampled by sequencing 46 unselected clones. These sequences showed that 8 of the 10 positions were incorporated in over 35% of the sequences, with an average incorporation of 47.8% for these eight crossover oligos. Crossovers 1 and 6 had incorporations of 12 and 15% respectively.

To enable the MLE genes to recombine at specific positions, we designed a series of crossover oligonucleotides with a 5' half identical to the sequence of one parent and a 3' half identical in sequence to a second parent. We included 60 such oligonucleotides in a recombination reaction containing all 3 MLEs to facilitate recombination at the 10 positions shown in FIG. 2B. We assessed the frequency of crossover incorporation in the shuffled library by sequencing 71 variants chosen randomly. The individual crossover oligonucleotides varied in the efficiency with which they were incorporated, being represented in between 20% and 50% of functionally unselected variants with 97% of the progeny incorporating at least one crossover.

Our analysis of the naive library also showed the library to be somewhat biased in sequence, with one parent, MLE I from *A. calcoaceticus*, contributing an average of only 4% of the final sequences. We believe that this is probably due to the much lower GC content of this parental gene (45% compared with 64% and 68% respectively for *P. putida* MLE I and MLE II). Such biases in recombination can be removed by resynthesizing genes with more similar codon usages, but we do not believe that this affects the conclusions that we have drawn from the present study.

Generation of Active Chimeric Enzymes

We transformed the chimeric enzyme library into an MLE-deficient *Acinetobacter* strain, and selected complementing clones as described in the Experimental Protocols (below). Bacterial colonies appeared between 1 and 6 days, from which we rescued and sequenced 332 independent MLE genes. In the 403 variants sequenced, both selected and unselected, we saw recombination between parents exclusively mediated by crossover oligonucleotides.

In the 332 active variants sequenced we found a total of 33 unique recombinant sequences. The majority of chimeric sequences incorporated a single segment (usually between 30 and 60 amino acids) from one parent into the backbone of a second parent, although six of the 33 incorporated over 100 residues from different parents. These results show that many different segments from structurally and functionally conserved proteins can functionally replace one another despite low sequence identities.

Computational Modelling Predicts Crossover Preferences in Functional Enzymes

We saw strong biases in crossover positions found in active chimeras. We measured these biases by comparing the frequency of each crossover in the 71 unselected chimeras with the frequency seen in the 33 unique active chimeras. We have assessed the predictive value of the contact energy curve by correlating the modeled energetic favorability of a crossover with its representation in active variants. For the 7 crossovers located within the α/β barrel, the correlation coefficient is 0.94, indicating that our algorithm is an effective pre-screen for productive crossover sites within this region.

The three positions outside the α/β barrel (98, 119 and 328) are all greatly under-represented in functional chimeras, although they are predicted to be energetically favorable. One possible reason for this domain-based distinction is the octomeric quaternary structure of active MLE: the majority of the oligomeric interactions involve the N-terminal domain. When we included oligomeric contact energies in our model we obtained data very similar to that shown in FIG. 2, but it is possible that contacts required for the retention of a stable quaternary structure should be more heavily weighted than intramolecular contacts. An alternative possibility is that the N-terminal domain on these proteins is thought to participate in binding interactions. There is no substrate-bound structure available for MLE, but analysis of an homologous protein, o-succinyl benzoate synthetase, shows that this "capping" domain performs a fairly large-scale movement of ~10 Å following ligand binding (Thompson, T. B. et al. (2000) "Evolution of enzymatic activity in the enolase superfamily: Structure of o-succinylbenzoate synthase from *Escherichia coli* in complex with Mg2+ and o-succinylbenzoate." *Biochemistry* 39: 10662-10676). Structural modeling can identify chimeras in which packing interactions will be maintained, but more computationally-intensive techniques such as molecular dynamics simulations can be used to assess whether a chimera will accommodate catalysis-related structural changes (Wang, W., Donini, O., Reyes, C. M. & Kollman, P. A. (2001) "Biomolecular simulations: recent developments in force fields, simulations of enzyme catalysis, protein-ligand, protein-protein, and protein-nucleic acid non-covalent interactions." *Annu. Rev. Biophys. Biomol. Struct.* 30: 211-243).

The Fastest Growing Strains Contain MLE Enzymes with composite Active Sites

We saw a large range of transfomant growth rates conferred by expression of the chimeric MLEs, with colonies appearing on selection plates between one and six days after transformation, as compared with two to four days for the three parental enzymes. Two progeny clones grew significantly more rapidly than the parents, taking less than a day to form colonies. One of these expressed a chimeric protein consisting mainly of *P. putida* MLE II, with sections of *A. calcoaceticus* MLE I (from 172 to 201), and *P. putida* MLE I (from 201 to 228). The resultant chimeric active site comprises residues from all three parents: including the functionally important residues Lys167, Lys169, and Asp249 contributed by *P. putida* MLE II, Asp 198 by *A. calcoaceticus* MLE I, and Glu224 by *P. putida* MLE I. The sequence of the chimeric enzyme from the other rapidly growing transformant was predominantly derived from *P. putida* MLE I, but again contains *A. calcoaceticus* MLE I residues between 172 and 201, both of which were predicted to be very favorable crossover positions by the in silico algorithm.

Our analysis of these most active chimeras illustrates the robustness of the α/β barrel structure. Of the three crossovers in chimera 1, only that at position 201 coincides with a stretch of more than two identical amino acids. The two substituted regions from *A. calcoaceticus* MLE I and *P. putida* MLE I share 13 and 11 identical amino acids with the corresponding 29 and 28 amino acid stretches of *P. putida* MLE II, which makes up the majority of the protein. These differences are not in general conservative changes, and it would be difficult to computationally design so many changes into so small a region of an enzyme's active site by previously described methods while retaining activity.

Computational Pre-Screening

In the results presented herein we have described an algorithm which allows us to pre-screen recombination sites before the physical construction of genes or libraries. The algorithm creates recombinant proteins in silico, predicts energy changes in the resulting chimeric molecules based on their deviations from a structurally characterized reference protein, and selects crossover sites likely to minimize the disruption of packing interactions.

In previous work, libraries of chimeric proteins have been produced physically by creating a single randomly positioned recombination event to generate a fusion between the N-terminus of one parent and the C-terminus of a second (Ostermeier, M., Shim, J. H. & Benkovic, S. J. (1999) "A combinatorial approach to hybrid enzymes independent of DNA homology." *Nature Biotechnol.* 17: 1205-1209; and Sieber, V., Martinez, C. A. & Arnold, F. H. (2001) "Libraries of hybrid proteins from distantly related sequences." *Nature Biotechnol.* 19: 456-460). These methods have produced relatively few functional chimeras with low activities.

Such random recombinants are functionally unimpressive: the best ITCHY chimeras had 500- to 10,000-fold lower activity than the starting genes. These include the possible introduction of reading frame shifts or insertions/deletions. Alternatively, because the selection step occurs following creation of chimeras with a single crossover, this could possibly lead to formation of unstable chimeras. The contact energy-based algorithm predicts that single crossover events will produce less stable chimeras than double crossovers (data not shown). Also, consistent with this argument is the fact that only one of the 33 active chimeras that we analyzed in this work had a single crossover; the rest resulted from multiple recombination events. Multiple crossovers are also found in the most active recombinants selected from previous family recombination work (see, for example, Crameri, 1998; Ness, 1999; Chang 1999; and Soong, N. et al., 2000, all supra ). Additionally, 81% of our active chimeras had fewer than 70 amino acids incorporated from another parent. Selecting chimeras with single crossover sites would limit the possibilities for these one-parent dominated chimeras to a crossover position in either the N- and C-terminal regions. Finally, by performing initial selection on chimeras with a single crossover may prematurely eliminate crossover sites that could function well in combination with other crossovers (Lutz, S., Ostermeier, M., Moore, G. L., Maranas, C. D. & Benkovic, S. J. (2001 "Creating multiple-crossover DNA libraries independent of sequence identity." *Proc. Natl. Acad. Sci. U S A.* 98 11248-11253). In contrast, our computational pre-screen can, in principle, consider as many recombination events as are desired.

Another approach to creating chimeras from highly divergent parents is that of semi-rational design, in which structural and functional information are combined and often coupled with some degree of sequence randomization and/or recombination. These experiments have generally been more successful than recombination with low sequence identity libraries, and have achieved changes in both substrate specificity and thermostability (see, for example, Altamirano, M. M., Blackburn, J. M., Aguayo, C. & Fersht, A. R. (2000) "Directed evolution of new catalytic activity using the alpha/beta-barrel scaffold." *Nature* 403: 617-622; Jermutus, L., Tessier, M., Pasamontes, L., van Loon, A. P. & Lehmann, M. (2001) "Structure-based chimeric enzymes as an alternative to directed enzyme evolution: phytase as a test case." *J. Biotechnol.* 85: 15-24; and Kaneko, S. et al. (2000) "Module recombination of a family F/10 xylanase: replacement of modules M4 and M5 of the FXYN of *Streptomyces olivaceoviridis* E-86 with those of the Cex of *Cellulomonas fimi.*" *Protein Eng.* 13: 873-879). Generation of chimeras in this way, however, requires considerable understanding of the structure-function relationships pertinent to the specific protein being modified.

SUMMARY OF EXAMPLE

In this example, we have described a method that combines the general applicability of directed evolution techniques with the speed and power of computational analysis. The only structural information required for our in silico recombination and pre-screen is three-dimensional structural information, such as a crystal structure of one of the parental proteins, an NMR structure, structure homology modeling information, or other structural determinations known to one of skill in the art. Thus, the approach is both generic and highly automatable. Optionally, the chimeras that pass this initial screen are synthesized and tested physically. While in this work we synthesized chimeric libraries using crossover oligonucleotides, any format which allows incorporation of pre-screening data (for example, synthetic recombination as described in Ness et al. (2002) Nature Biotechnology 20:1251-1255, WO 00/42561, and WO 00/42560) can be employed. By removing poorly-folded variants, the number of proteins that must be physically screened can be reduced, increasing the likelihood of success, particularly in cases where screens are laborious, complex and time consuming. As our understanding of the relationship between structure and function improves, we expect that the range of properties that can be evaluated by computational approaches will expand, thereby enhancing the value of in silico pre-screening algorithms.

We obtained five recombination products whose sequences differ from the closest parent by at least 70 amino acids; these chimeric biomolecules all contain crossovers predicted to be favorable by the in silico algorithm. By using diversity selected from parental sequences that have already been screened by natural evolution for their ability to fold into the same functional structure, we can use a simple computational pre-screen to design new sequences that are very different from any starting point. Furthermore, by coupling this algorithm with crossover oligonucleotide-mediated recombination we have produced a chimeric library containing functionally active chimeras generated from sequences with as little as 40% sequence identity.

The chimeric library was grown in an MLE knockout strain on plates that require MLE activity for growth. The colonies grew over 2-7 days and 124 of the selected colonies were sequenced. Out of these sequenced selected clones there were many repeated sequences resulting in 33 unique shuffled sequences. Three of the selected sequences incorporated over 100 residues from different parents, but the majority of chimeric sequences incorporated between 30-60 residues. We see strong patterns in which crossover positions were incorporated into the selected versus the unselected sequences with positions 119, 144, 172, and 201 dominating.

The prediction trends remain very similar over the varying lengths with the optimal starting residues 119, 144, 172, 302, and 328. We see that crossovers at positions 119, 144, 172, and 328 were predicted correctly as they are seen far more often in the selected versus unselected clones. Only two positions, 98 and 302, did not follow the predictions and were not seen as often as expected. Position 98 is only seen 12% of the unselected clones, therefore the lack of this oligo incorporation overall could explain the discrepancy between predicted and actual results. The optimal ending residues are predicted to be 144, 172, 201, and 228. We found that the likely sites to end crossovers were at positions 172, 201 and 302. Position 228 was only incorporated in 15% of the unselected clones and could therefore explain why this crossover was not seen in the selected clones. Position 144 was predicted to be very favorable but was only seen ending crossovers in a small number of selected clones. This could be due to the small number of clones that initiated crossovers at position 98 and 119 thus limiting the number of crossovers that could end at position 144.

Experimental Protocols

Wild type genes for MLE I and 2 from *P. putida* and the MLE I from *A. calcoaceticus*, were amplified and fragmented as previously described (Crameri et al., 1998). Oligonucleotides complementary to one parent at the 3' end and to another parent at the 5' end were ordered from QUIAGEN Operon (Alameda, Calif.), with the break points corresponding to the positions identified in the text. The mixture of fragments and oligos were assembled as described, e.g., in Ness et al. "Synthetic shuffling expands functional protein diversity by allowing amino acids to recombine independently" (2002) Nature Biotechnology 20:1251-1255, and WO98/27230. The resulting chimeric sequences were cloned into a vector as described below. Sequencing of the unselected and selected chimeric sequences was performed on an Applied Biosystems 3700 Sequencer (Foster City, Calif.).

Selection for MLE Activity

An *Acinetobacter calcoaceticus* MLE I knockout was constructed using natural competence and homologous recombination to replace the catB gene with a kanamycin-resistance cassette. Briefly, forward and reverse primers were used to PCR amplify the kanamycin-resistance cassette of pACYC177 (with promoter). Both PAGE-purified primers were 100 nucleotides in length with 20 nucleotides of 3' end identity just upstream (forward primer) or downstream (reverse primer) of the kanamyacin-resistance cassette and 80 nucleotide tails with identity to regions just upstream (forward primer) or downstream (reverse primer) of the *Acinetobacter* ADP1 catB gene (Genebank AF009224), which codes for muconate lactonizing enzyme, MLE I.

*A. calcoaceticus* strain ATCC 33305 (strain BD413) was grown overnight at 30° C. A volume of 0.4 ml was subcultured into 10 ml LB in a 50 ml tube, then shaken for 2 hours at 30° C. and 300 rpm. Approximately 0.5 ml of culture was mixed with 50 µl of PCR reaction amplifying the kanamycin cassette. Kanamyacin-resistant transformants were selected on LB agar with 40 µg/ml kanamycin and streaked for the ability to grow on benzoate agar. Benzoate agar was prepared using a 10× mineral salts base consisting of 10 g $K_2SO_4$, 135 g $K_2HPO_4$, 47 g $KH_2PO_4$, 25 g of NaCl, 5.4 g $NH_4Cl$ and 50 ml of 2% $MgSO_4 \times 7H_2O$ per liter and a 1000× trace salts solution consisting of 10 mM $CaCl_2$, 0.5 mM $FeCl_3$, and 0.5 mM $MnCl_2$. In addition to the mineral salts base and trace elements, 2.5 ml of 1 M $Na_2MoO_4 \times 2H_2O$ and 2.5 ml of 1M Sodium Benzoate were added per liter along with Difco Bacto agar to 1.5%). One transformant, designated NS238, which was unable to grow with benzoate was used to select for active chimeras.

The wild type genes for MLE I and 2 from *P. putida* and the MLE I from *A. calcoaceticus* were cloned into the broad host range vector pMMB66EH (ATCC 37620). These three constructs were able to complement the knockout strain NS238 for growth on benzoate agar. Libraries of chimeric MLEs, as described above, were cloned into plasmid pMMB66EH, transformed into strain NS238 using natural competence, plated to benzoate agar formulated with 0.15 mM IPTG and incubated up to 1 week at 37° C. The growth phenotypes of benzoate-utilizing transformed cells were examined by streaking for single colonies to benzoate agar and following growth relative to the three wild type genes over a period of 6 days at 37° C.

Structural Modeling

The interacting residues in the MLE 1p structure, 1MUC, were used to define the contact map of the enzyme using the MOE software from the Chemical Computing Group (Montreal, Quebec, Canada). The contact map is a matrix (C) describing the interactions within the crystal structure such that for residues i and j, scored such that Cij=1 if there is a potential hydrogen bond partner or hydrophobic interaction within a distance of 4.5 Å between the two residues and Cij=0 if not.

All possible two-crossover chimeras were generated in silico for the three MLE parents. These chimeras were then evaluated in comparison to the original contact map. Using the potentials of Miyazawa and Jernigan, the contact energy of the chimeras was calculated. At each position of interaction in the MLE structure, the Miyazawa Jernigan energy for the contacting residues in the in silico derived chimera was summed to generate the total contact energy (Ec).

$$Ec = \sum_i \sum_{j \neq i} E_{MJ}(i, j) * (C_{ij}) \qquad \text{Eqn 1}$$

where $E_{MJ}(i,j)$ is the Miyazawa-Jernigan energy for residues i and j and $C_{ij}$ is 1 if there is a contact between i and j and 0 if there is no contact. Note that as the length of the replacement segment increases, the contact energy also increases. This is due to increased differences between the chimeras and the original contact map. We therefore limited our crossover analysis to replacement lengths of 80 and less to minimize this bias towards the reference sequence. Relevant descriptions of the Miyazawa and Jernigan potentials are found in the references identified above: For amino acid sequences, the contact energies can be estimated, for example, using a Miyazawa-Jernigan energy matrix (see, for example, Miyazawa and Jernigan (1999) "Self-consistent estimation of inter-residue protein contact energies based on an equilibrium mixture approximation of residues" Proteins 34: 49-68); Miyazawa and Jernigan (1999) "An empirical energy potential with a reference state for protein fold and sequence recognition" Proteins 36: 357-69; Zhang (1998) "Extracting contact energies from protein structures: a study using a simplified model" Proteins 31: 299-308; and Miyazawa, S. & Jernigan, R. L. (1996) "Residue-residue potentials with a favorable contact pair term and an unfavorable high packing density term, for simulation and threading." *J. Mol. Biol.* 256: 623-464.

We also tested a much more computationally intensive algorithm in which chimeric sequences were threaded through a reference structure and then subjected to energy-minimization routines using the AMBER94 forcefield through the Molecular Operating Environment from the Chemical Computing Group. Initial results using this method were not significantly different from the much simpler and computationally faster $\Delta E_C$ calculation.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of selecting crossover points between two or more biomolecules, the method comprising:
   i) providing a reference sequence of a reference biomolecule;
   ii) generating a contact map for the reference sequence, the contact map identifying proximal elements of the reference sequence;
   iii) providing a first sequence of a first biomolecule and a second sequence of a second biomolecule, between which one or more crossover points are to be determined;
   iv) aligning the first sequence and the second sequence with the reference sequence and selecting a crossover point between a first subsequence from the first sequence and a second subsequence from the second sequence;
   v) replacing the first subsequence from the first sequence with the second subsequence from the second sequence to produce a chimeric biomolecule sequence, wherein the first subsequence of the first sequence and the second subsequence of the second sequence terminate at the selected-crossover point;
   vi) aligning the chimeric biomolecule sequence with the reference sequence and arranging the chimeric biomolecule sequence in the contact map for the reference sequence to select two or more elements in the chimeric biomolecule sequence that correspond to the proximal elements of the reference sequence such that the alignment between the chimeric biomolecule sequence and the reference sequence is preserved during selection of the two or more elements; and
   vii) scoring the two or more elements selected in vi) by considering the interaction of said elements with one another, wherein scoring provides a measure of the likelihood of a new biomolecule comprising the two or more elements having a property similar or identical to the reference biomolecule,
   wherein at least operation iv) is performed by executing instructions on a computer system programmed to perform said operation.

2. The method of claim 1, wherein the biomolecules comprises polypeptides or proteins and the elements comprise amino acid residues.

3. The method of claim 1, wherein the biomolecules comprise nucleic acids and the elements comprise nucleotides.

4. The method of claim 1, wherein the reference sequence is the first sequence.

5. The method of claim 1, wherein generating the contact map comprises determining one or more spacings of elements in the biomolecule and identifying two or more proximal elements within a critical distance of one another.

6. The method of claim 5, wherein the critical distance ranges from about 2 Angstroms to about 6.5 Angstroms.

7. The method of claim 5, wherein the critical distance is less than about 4.5 Angstroms.

8. The method of claim 1, wherein providing the first sequence and the second sequence comprises providing amino acid sequences or nucleic acid sequences for two proteins having an amino acid sequence identity of about 60% or less as determined using a BLASTP algorithm and default parameters.

9. The method of claim 1, wherein the property similar or identical to the reference biomolecule comprises an enzyme activity or a protein stability.

10. The method of claim 1, wherein scoring comprises calculating the contact energy of the two or more selected elements in the chimeric biomolecule sequence.

11. The method of claim 10, wherein the contact energy is calculated using a Miyazawa-Jernigan energy matrix.

12. The method of claim 1, wherein scoring comprises presenting the score in a triangular contour plot.

13. The method of claim 1, further comprising synthesizing one or more chimeric biomolecules.

14. The method of claim 13, wherein synthesizing the one or more chimeric biomolecules comprises providing one or more recombinant constructs.

15. The method of claim 13, wherein synthesizing the one or more chimeric biomolecules comprises performing one or more recombination processes upon two or more parental sequences, thereby generating one or more recombinant constructs encoding the chimeric biomolecule.

16. The method of claim 13, further comprising assaying the one or more chimeric biomolecules.

17. A non-transitory computer-readable medium comprising computer code for:
   i) inputting a reference sequence of a reference biomolecule;
   ii) generating a contact map for the reference sequence, the contact map identifying proximal elements of the reference sequence;
   iii) aligning the first sequence and the second sequence with the reference sequence and selecting a crossover point between a first subsequence from the first sequence and a second subsequence from the second sequence;
   iv) replacing the first subsequence from the first sequence with the second subsequence from the second sequence to produce a chimeric sequence, wherein the first subsequence of the first sequence and the second subsequence of the second sequence terminate at the selected crossover point;
   v) aligning the chimeric biomolecule sequence with the reference sequence and arranging the chimeric biomolecule sequence in the contact map for the reference sequence to select two or more elements in the chimeric biomolecule sequence that correspond to the proximal elements of the reference sequence such that the alignment between the chimeric biomolecule sequence and the reference sequence is preserved during selection of the two or more elements; and
   vi) scoring the two or more selected elements by considering the interaction of said elements with one another, wherein the scoring provides a measure of the likelihood of a new biomolecule comprising the two or more selected elements having a property similar or identical to the reference biomolecule.

18. The computer-readable medium of claim 17, wherein the computer code comprises code for repeating iv) through vi) for at least one additional crossover site.

19. The computer-readable medium of claim 17, wherein (i) comprises code for providing the amino acid sequence of a known biomolecule or providing the nucleic acid sequence encoding the known biomolecule.

20. The computer-readable medium of claim 17, wherein (i) comprises code for querying a nucleic acid or biomolecule database.

21. The computer-readable medium of claim 17, wherein the code for generating a contact map comprises code for determining amino acid spacing from a crystallographic model or an NMR model of the reference biomolecule and identifying residues within a critical distance of each other.

22. The computer-readable medium of claim 17, wherein the generating a contact map comprises determining amino acid spacing from an protein-folding analysis of the reference biomolecule and identifying residues within a critical distance of each other.

23. The computer-readable medium of claim 21, wherein the critical distance varies with the nature of the amino acid-amino acid interaction.

24. The computer-readable medium of claim 21, wherein the critical distance is less than about 4.5 Angstroms.

25. The computer-readable medium of claim 17, wherein the code for aligning a first and a second amino acid sequence comprises code for querying a nucleic acid or protein database.

26. The computer-readable medium of claim 17, wherein the code for scoring comprises code for calculating the contact energy of a pair of amino acids in a chimeric amino acid sequence where that pair of residues corresponds to residues that are in contact in the contact map.

27. The computer-readable medium of claim 17, wherein the code for scoring comprises code for summing the contact energy for all of the residues in the chimeric amino acid sequence that correspond to residues that are in contact in the contact map.

28. The computer-readable medium of claim 17, wherein the code for scoring comprises code for calculating a contact energy of interacting residues using a Miyazawa energy matrix.

29. The computer-readable medium of claim 17, wherein the code for scoring comprises code for presenting the score to a user in a graphical user interface.

30. The computer-readable medium of claim 17, wherein the code for scoring comprises code for presenting the score in a triangle plot.

31. An integrated system for assessing crossover sites, comprising:
   the computer readable medium of claim 17; and
   a graphical interface.

* * * * *